US009549958B2

(12) United States Patent
Sheu et al.

(10) Patent No.: US 9,549,958 B2
(45) Date of Patent: Jan. 24, 2017

(54) **EXTRACTS OF *CYNANCHUM* SP. AND ACTIVE INGREDIENTS CONTAINED THEREIN IN USE OF ARTHRITIS TREATMENT**

(75) Inventors: Jennline Sheu, Hsinchu (TW);
Lain-Tze Lee, Hsinchu (TW);
Ying-Chu Shih, Hsinchu County (TW);
Cheng-Yu Lee, Hsinchu (TW);
Yi-Ching Lee, Hsinchu (TW);
Jir-Mehng Lo, Hsinchu County (TW);
Tien-Soung Tong, Taichung (TW);
Jui-Hung Yen, New Taipei (TW);
Kuo-Kuei Huang, Hsinchu County (TW); Ying-Fei Tsai, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 270 days.

(21) Appl. No.: 14/114,463

(22) PCT Filed: Apr. 27, 2012

(86) PCT No.: PCT/CN2012/074815
§ 371 (c)(1),
(2), (4) Date: Jan. 10, 2014

(87) PCT Pub. No.: WO2012/146194
PCT Pub. Date: Nov. 1, 2012

(65) Prior Publication Data
US 2014/0134280 A1     May 15, 2014

Related U.S. Application Data

(60) Provisional application No. 61/480,550, filed on Apr. 29, 2011.

(30) Foreign Application Priority Data

Apr. 27, 2012  (CN) .......................... 2012 1 0128430

(51) Int. Cl.
| A61K 36/00 | (2006.01) |
| A61K 31/44 | (2006.01) |
| A61K 36/24 | (2006.01) |
| C07D 471/04 | (2006.01) |
| A61K 31/437 | (2006.01) |
| A61K 36/27 | (2006.01) |

(52) U.S. Cl.
CPC ............ *A61K 36/24* (2013.01); *A61K 31/437* (2013.01); *A61K 36/27* (2013.01); *C07D 471/04* (2013.01)

(58) Field of Classification Search
None
See application file for complete search history.

(56) References Cited

U.S. PATENT DOCUMENTS

| 5,683,697 A | 11/1997 | Tani |
| 5,852,221 A | 12/1998 | Kashihara et al. |
| 6,984,405 B1 | 1/2006 | Kim |
| 7,569,238 B2 | 8/2009 | Ko et al. |
| 7,652,027 B2 | 1/2010 | Lee et al. |
| 7,763,284 B2 | 7/2010 | Kim |
| 7,838,048 B2 | 11/2010 | Sheu et al. |
| 2008/0176886 A1 | 7/2008 | Lee et al. |

FOREIGN PATENT DOCUMENTS

| CA | 2740810 | 4/2010 |
| CN | 1321642 A | 11/2001 |
| CN | 1371731 A | 10/2002 |
| CN | 1742884 A | 3/2006 |
| CN | 1742908 A | 3/2006 |
| CN | 1742961 A | 3/2006 |
| CN | 1813976 A | 8/2006 |
| CN | 1814051 A | 8/2006 |
| CN | 1814056 A | 8/2006 |
| CN | 1814180 A | 8/2006 |
| CN | 101021029 A | 8/2007 |
| CN | 101024065 A | 8/2007 |
| CN | 101837081 A | 9/2010 |
| CN | 101948470 A | 1/2011 |
| CN | 101962381 A | 2/2011 |
| JP | 2003-137776 A | 5/2003 |
| JP | 2006-22002 A | 1/2006 |
| JP | 2007-210993 A | 8/2007 |
| KR | 2001-0067023 A | 7/2001 |
| KR | 2003-0016774 A | 3/2003 |
| KR | 10-2005-0007996 A | 1/2005 |
| KR | 10-2012-0010026 A | 2/2012 |
| WO | WO 01/23384 A1 | 4/2001 |

(Continued)

OTHER PUBLICATIONS

Capo et al. (1989) Journal of Natural Products, vol. 52, No. 2, pp. 389-390.*
Gibson et al. (2011) J. Chem. Ecol. 37: 871-879.*
Konda et al. (1992) J. Natural Prods. vol. 55, No. 8. pp. 1118-1123.*
Konda et al. (1992) J. Nat. Prods. vol. 55, No. 10., pp. 1447-1453.*
Mogg et al. (2008) Biochemical Systematics and Ecology 36: 383-391.*
Shan et al. (2006) J. Ethnopharmacology 107: 389-394.*
Choi et al., "The Anti-inflammatory and Anti-nociceptive Effects of Ethyl Acetate Fraction of Cynanchi Paniculati Radix", Biol. Pharm. Bull., 2006, 29(5), pp. 971-975.
Damu et al., "Cytotoxic Phenanthroindolizidine Alkaloids from the Roots of Ficus septica", Planta Medica, 2009, 75(10), pp. 1152-1156.

(Continued)

*Primary Examiner* — Chris R Tate
*Assistant Examiner* — Russell Fiebig
(74) *Attorney, Agent, or Firm* — Birch, Stewart, Kolasch & Birch, LLP

(57) ABSTRACT

An extract of *Cynanchum* sp. in use of arthritis treatment is provided. The extract of *Cynanchum* sp. and an active ingredient contained therein, antofine, are applicable to a method, pharmaceutical composition and dietary supplement for treatment of arthritis. A mass production of antofine from plant extracts is also provided.

5 Claims, 17 Drawing Sheets

(56) References Cited

FOREIGN PATENT DOCUMENTS

| WO | WO 2006/003676 A1 | 1/2006 |
|---|---|---|
| WO | WO 2007/046113 A2 | 4/2007 |

OTHER PUBLICATIONS

German Office Action dated Oct. 7, 2014, issued in German Patent Application No. DE 112012000221.0.
Japanese Office Action dated Jan. 6, 2015, issued in Japanese Patent Application No. JP 2014-506745.
Kosuge et al., "Studies on Bioactive Substances in the Chinese Material Medicines Used for Arthritic Diseases in Traditional Chinese Medicine. I. Anti-inflammatory and Analgesic Effect of Chinese Material Medicines Used for Arthritic Diseases", Yakugaku Zasshi, 1985, 105(9), pp. 845-847.
Weigrebe et al., "Alkaloide aus Cynanchum vincetoxicum (L.) Pers.", Liebigs Ann. Chem., 1969, 721, pp. 154-162.
Japanese Office Action for Japanese Application No. 2014-506745, dated Sep. 8, 2015, with an English translation.
Capo, M. et al. "(--)-Antofine: A Phenanthroindolizidine from Vincetoxicum nigrum," Journal of Natural Products, 1989, vol. 52, No. 2, pp. 389-390.
Fu, Y. et al. "Synthesis and structure—activity studies of antofine analogues as potential anticancer agents," Bioorganic & Medicinal Chemistry Letters, 2007, vol. 17, No. 1, pp. 97-100.
Furstner, A. et al. "Total Syntheses of the Tylophora Alkaloids Cryptopleurine, (—)-Antofine, (-)-Tylophorine, and (-)-Ficuseptine C," Chemistry—A European Journal, Sep. 2006, vol. 12, No. 28, pp. 7398-7410.
Gao, W. et al. "Structural analogs of tylophora alkaloids may not be functional analogs," Bioorganic & Medicinal Chemistry Letters, 2008, vol. 18, No. 2, pp. 704-709.
International Search Report issued in PCT/CN2012/074815 mailed Aug. 2, 2012.
Kim, S. "First Asymmetric Total Synthesis of (-)-Antofine by Using an Enantioselective Catalytic Phase Transfer Alkylation," Organic Letters, 2003, vol. 5, No. 15, pp. 2703-2706.
Lebrun, S. et al. "Total Syntheses of (±)-Cryptopleurine, (±)Antofine and (±)Deoxypergularinine," Tetrahedron, 1999, vol. 55, No. 9, pp. 2659-2670.
Lou H. et al. "Alkaloids from the roots of Cynanchum hancockianum and their derivatives preparation," Acta Academiae Medicinae Shandong, Jun. 1995, vol. 33, No. 2, pp. 158-162.
Min, H. et al. "Inhibition of cell growth and potentiation of tumor necrosis factor-$\alpha$(TNF-$\alpha$)-induced apoptosis by a phenanthroindolizidine alkaloid antofine in human colon cancer cells," Biochemical Pharmacology, 2010, vol. 80, No. 9, pp. 1356-1364.
Min, H. et al. "Inhibition of Lipopolysaccharide-Induced Nitric Oxide Production by Antofine and Its Analogues in RAW 264.7 Macrophage Cells," Chemistry & Biodiversity, Feb. 2010, vol. 7, No. 2, pp. 409-414.
Mogg, C. et al. "Tests of the antibiotic properties of the invasive vine Vincetoxicum rossicum against bacteria, fungi and insects," Biochemical Systematics and Ecology, 2008, vol. 36, pp. 383-391.
Office Action issued in Chinese Patent Application No. 201210128430.2 dated Jul. 8, 2013.
Office Action issued in Taiwan Patent Application No. 100149768 dated Jul. 15, 2013.
Qi, L. et al. "Study on Alkaloids of Cynanchum Komarrivii Al Iljiniski Widely Grown in Ningxia," Journal of Ningxia Medical College, 2002, vol. 24, No. 5, pp. 336-339.
Qi, L. et al. "Study on Pharmacological Action of Alkaloids of Cynanchum Komarovii Al Iljiniski Widely Grown in Ningxia," Journal of Ningxia Medical College, Dec. 2002, vol. 24, No. 6, pp. 398-399.
Shen, Y. et al. "Study on Analgesic, Anti-inflammatory and Anti-thrombotic Effects of Rhizoma Cynanchi Stauntonii," China Pharmacy, 2001, vol. 12, No. 1, pp. 15-16.
Staerk, D. et al. "In Vitro Cytotoxic Activity of Phenanthroindolizidine Alkaloids from Cynanchum vincetoxicum and Tylophora tanakae against Drug-Sensitive and Multidrug-Resistant Cancer Cells," Journal of Natural Products, 2002, vol. 65, No. 9, pp. 1299-1302.
Staerk, D. et al. "Phenanthroindolizidine alkaloids from Vincetoxicum pumilum," Biochemical Systematics and Ecology, 2005, vol. 33, pp. 957-960.
Su, C. et al. "Total synthesis of phenanthroindolizidine alkaloids (±)-antofine, (±)-deoxypergularinine, and their dehydro congeners and evaluation of their cytotoxic activity," Bioorganic & Medicinal Chemistry, Jun. 2008, vol. 16, No. 11, pp. 6233-6241.
Subramaniam, G. et al. "A benzopyrroloisoquinoline alkaloid from Ficus fistulosa," Phytochemistry Letters, 2009, vol. 2, No. 2, pp. 88-90.
Wang, H. et al. "Antitumor Constituents from the Roots of Tylophora floribunda," Chinese Journal of Natural Medicines, Sep. 2006, vol. 4, No. 5, pp. 352-354.
Written Opinion of the International Searching Authority issued in PCT/CN2012/074815 mailed Aug. 2, 2012.
Yang, C. et al. "Anti-Inflammatory Mechanisms of Phenanthroindolizidine Alkaloids," 2006, vol. 69, No. pp. 749-758.
Yang, W. et al. "Effects of Anti-inflammation and Ache Easing of Total Alkaloid of Cynanchum Komarovii Al Iljinski," Journal of Ningxia Medical College, Jun. 2005, vol. 27, No. 3, pp. 191-193.
Yang, W. et al. "Effects of Total Alkaloid of Cynanchum Komarovii Al. Iljinski on Inflammation Mediators in Adjuvant Arthritis Rats," Oct. 2009, vol. 31, No. 5, pp. 574-575.
Yang, W. et al. "Influence of Total Alkaloid of Cynanchum Komarovii Al Iljiniski on the Secondary Inflammation of Adjuvant Arthritis in Rats," Journal of Ningxia Medical College, Feb. 2007, vol. 29, No. 1, pp. 16-18.
Yao, Y. et al. "Determination of Chemical Structure of Phenanthroindolizidine Alkaloids Separated from Cynanchum Komarovii Al. Lljinski," Journal of Inner Mongolia Polytechnic University, 2001, vol. 20, No. 4, pp. 241-244.
You, X. et al. "Effects of a Novel Tylophorine Analog on Collagen-Induced Arthritis Through Inhibition of the Innate Immune Response," Arthritis & Rheumatism, Mar. 2006, vol. 54, No. 3, pp. 877-886.
Zhang, S. et al. "Study on Anti-inflammatory Effect of C21 Steroidal Glycoside from the Root of Cynanchum auriculatum planted in JiangSu," Modern Chinese Medicine, May 2007, vol. 9, No. 5, pp. 8-12.
Zhen, Y. et al. "Antitumor alkaloids isolated from Tylophora ovata," Acta Botanica Sinica, 2002, vol. 44, No. 3, pp. 349-353.

\* cited by examiner

_EXTRACTS OF CYNANCHUM SP. AND ACTIVE INGREDIENTS CONTAINED THEREIN IN USE OF ARTHRITIS TREATMENT_

CROSS REFERENCE TO RELATED APPLICATIONS

This application is the National Phase of PCT/CN2012/074815 filed on Apr. 27, 2012, which claims the priority under 35 U.S.C. 119(a) to China Patent Application No. 20121028430.2, filed Apr. 27, 2012, and which claims the priority under 35. U.S.C. 119(e) to U.S. Provisional Application No. 61/480,550 filed Apr. 29, 2011, the entireties of which are incorporated by reference herein.

TECHNICAL FIELD

The technical field relates to the treatment of arthritis.

BACKGROUND

Arthritis is predominantly a disease of the elderly and morbidity has increased with civilization. The treatment of arthritis includes administration of corticosteroids to eliminate inflammatory symptoms and inhibit the immune system, or administration of non-steroid anti-inflammatory drugs (NSAIDs), such as COX-1 inhibitors, COX-2 inhibitors, Celebrex or Ibuprofen, to ameliorate pain and inflammation. However, severe side effects and limited effects of these drugs drive new-generation of drugs to be developed.

The new-generation of drugs for the treatment of arthritis focus on the role of the cytokine, TNF-$\alpha$, during the development of arthritis. A series of bioagents to decrease the secretion of TNF-$\alpha$ in arthritis patients has been developed, like the anti-TNF-$\alpha$ antibody, Adalimumab and Infliximab, or TNF-$\alpha$ antagonist, Etanercept. Studies show that a combination of an immunoinhibitory agent, methotrexate, and the TNF-$\alpha$ antagonist, etanercept, may increase the treatment effect of arthritis (Tracey D, et al., Tumor necrosis factor antagonist mechanisms of action: a comprehensive review, Pharmacology & Therapeutics 117 (2008) 244~279.). The agents for inhibition of other cytokines, such as IL-6 antibodies and IL-$\beta$-ra, have also been known for the treatment of arthritis. However, the limited efficacy, side effects and single administration present in these agents has lead to an urgent desire to develop new drugs.

SUMMARY

In one embodiment of the invention provides a method for treatment of arthritis, comprising administrating an effective amount of an extract of _Cynanchum_ sp. to a subject in need thereof.

In another embodiment of the invention provides a pharmaceutical composition for the treatment of arthritis, comprising an extract of _Cynanchum_ sp. as an active ingredient or pharmaceutically acceptable carrier.

In one embodiment of the invention provides a method for treatment of arthritis, comprising administrating an effective amount of antofine to a subject in need thereof.

In another embodiment of the invention provides a pharmaceutical composition for the treatment of arthritis, comprising antofine as an active ingredient and a pharmaceutically acceptable carrier.

In one embodiment of the invention provides a method for the production of antofine, comprising the steps of: (i) mixing a plant powder with a first solvent to form a first blend; (ii) heating and filtering the first blend to obtain a first extract; (iii) concentrating the first extract and substantially adding an acid to form a suspension with a sticky material; (iv) filtering the suspension to remove the sticky material and obtain a clear solution; (v) extracting the clear solution with a second solvent to obtain a second extract solution; (vi) concentrating and purifying the second extract solution; wherein the plant is selected from the group consisting of at least one of _Albizzia julibrissin, Antitoxicum funebre, Cocculus laurifolius, Cocculus pendulus, Corydalis meifolia, Croton sparsiflours, Cryptocarya oubatchensis, Cryptocarya phyllostemon, Cryptocarya chinensis, Cynanchum hancockianum, Cynanchum inamoenum, Cynanchum komarovi, Cynanchum paniculatum, Cynanchum vincetoxicum, Ficus fistulosa, Ficus septica, Pergularia daemia, Stephania glabra, Tylophora floribunda, Tylophora indica, Tylophora tanakae, Vincetoxicum hirundinaria, Vincetoxicum nigrum, Vincetoxicum officinale, Vincetoxicum pumilu_ and _Vincetoxicum rossicum_.

In one more embodiment of the invention provides a dietary supplement comprising antofine as an active ingredient and a food additive.

In another embodiment of the invention provides a dietary supplement comprising an extract of _Cynanchum_ sp. as an active ingredient and a food additive.

DRAWINGS

The disclosure can be more fully understood by reading the subsequent detailed description and examples with references made to the accompanying drawings, wherein.

DETAILED DESCRIPTION

Figure 1:
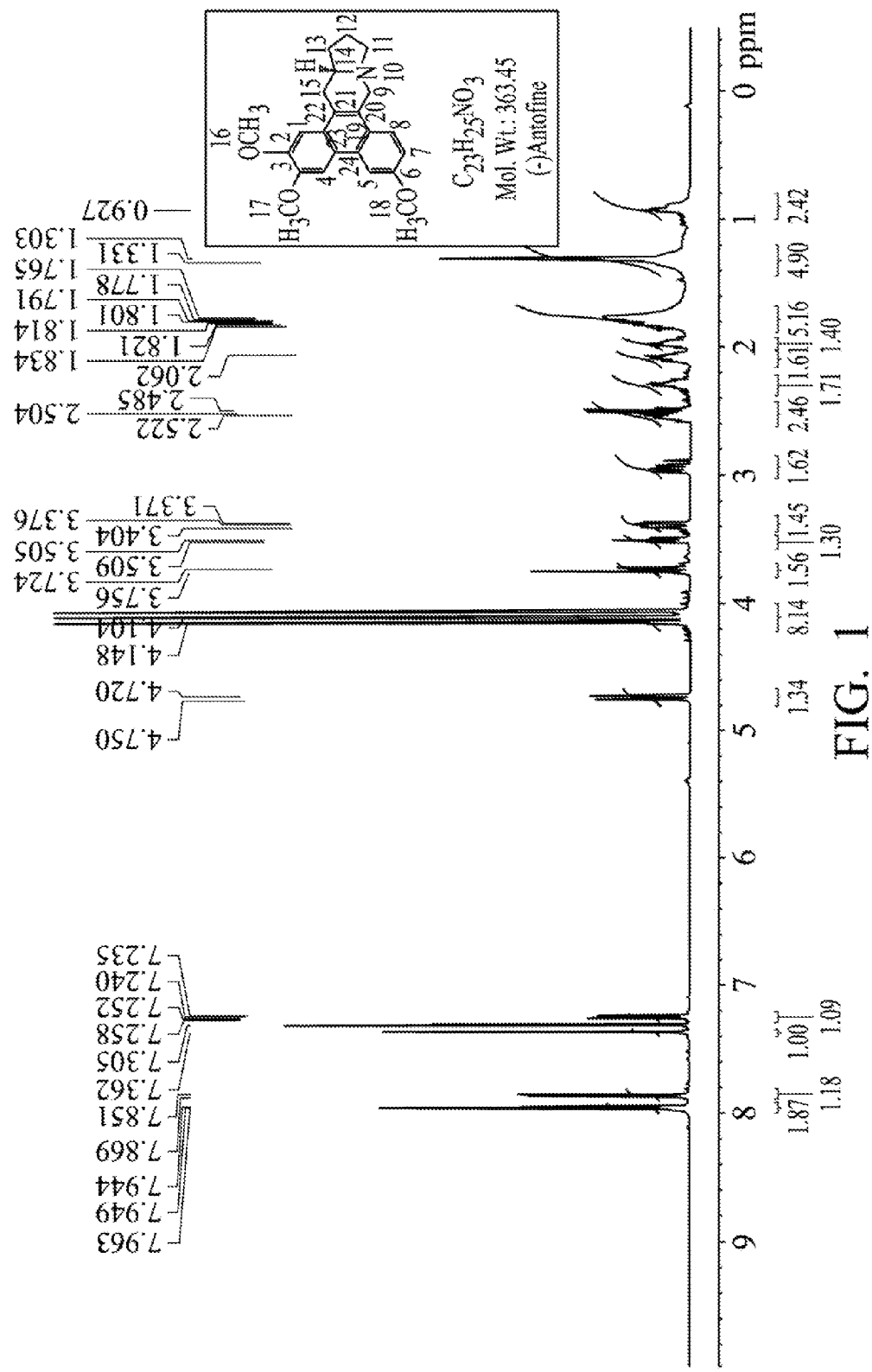
FIGS. 1 and 2 are the NMR data of crystals extracted from _Cynanchum hancockianum_, wherein the crystal from _Cynanchum hancockianum_ was identified as antofine.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

One embodiment of the invention provides a method for treatment of arthritis, comprising administrating an effective amount of an extract of *Cynanchum* sp. to a subject in need thereof. In another embodiment, the invention provides a pharmaceutical composition of the treatment of arthritis, comprising an extract of *Cynanchum* sp. as an active ingredient and a pharmaceutically acceptable carrier.

The *Cynanchum* sp. herein comprises *Cynanchum hancockianum, Cynanchum inamoenum, Cynanchum komarovii, Cynanchum paniculatum, Cynanchum vincetoxicum, Cynanchum atratum* or *Cynanchum stauntonii*, in which *Cynanchum hancockianum* is preferable.

The extraction of *Cynanchum* sp. according to one embodiment of the invention may be suitably adjusted depending on the plant species, the tissues for extraction or the like. In one embodiment of the invention, the extraction of *Cynanchum* sp. may comprise the steps of:

(i) mixing a plant powder with a first solvent to form a first blend;

(ii) heating and filtering the first blend to obtain a first extract;

(iii) concentrating the first extract and substantially adding an acid to form a suspension with a sticky material;

(iv) filtering the suspension to remove the sticky material and obtain a clear solution;

(v) extracting the clear solution with a second solvent to obtain a second extract solution; and (vi) concentrating and purifying the second extract solution.

More specific, the first solvent comprises water, alcohols, esters, ethers, ketones or a combination thereof. The alcohols recited in the first solvent may comprise methanol, ethanol, propanol, isopropanol, butanol, 2-butanol, 2-methylpropanol, 2-methyl-propan-2-ol, 1-pentanol, 2-pentanol, 3-pentanol, 1-hexanol, 2-hexanol, 3-hexanol or a combination thereof. The esters recited in the first solvent may comprise methyl acetate, ethyl acetate, propyl acetate, butyl acetate, pentyl acetate, hexyl acetate or a combination thereof. The ketones recited in the first solvent may comprise acetone, methyl ethyl ketone, 2-pentanone, 3-pentanone or a combination thereof. The ethers recited in the first solvent may comprise ether, propyl ether, isopropyl ether or a combination thereof.

In one example of the invention, the first solvent is a mixture solvent consisting of 80~100% by weight of butyl acetate and 0~20% by weight of ethanol. In another example of the invention, the first solvent is 50~100% by weight of isopropanol aqueous solution or 90~100% by weight of isopropanol aqueous solution.

According to the invention, the acid added into the first extract is not specifically limited, but hydrochloric acid is preferable. In one example of the invention, 0.1~2N hydrochloric acid is used.

According to one embodiment of the invention, the heating temperature in the step (ii) is from room temperature to boiling temperature of the blend. The heating duration may last 2 hours or more. In one example, the heating temperature is 25~75° C. and 70~75° C. is preferable.

According to one embodiment of the invention, the second solvent may comprise dichloromethane, methanol, ethanol, ether, acetone or a combination thereof, preferably dichloromethane, but it is not limited. The extraction with the second solvent may be preformed at least one time for an increase of the purity. Preferably, the extraction with the second solvent may be performed in one to three times, but not limited thereto.

According to one embodiment of the invention, the purifying in the step (vi) may comprise column chromatography or recrystallization, but it is not limited. The recrystallization may comprise the steps of mixing the concentrated or dried extract with a polar solvent and, after heating and dissolution, cooling down the solution for crystallization. The polar solvent may comprise dichloromethane, methanol, ethanol, ether, acetone or a combination thereof. In one example, dichloromethane is used.

The column chromatography herein refers to a method for separating a component in a mixture by an elute driving the mixture through a column fulfilled with absorbable solid fillers. Because the components in the mixture have different affinities to the fillers of the column and have different solubility to the elute, the components pass through the column with varied velocities and, therefore, are separated. The elute may comprise methanol, ethanol, ethyl acetate, butyl acetate, or a combination thereof. One example of the invention use silica column chromatography with elute consisting of ethyl acetate and methanol in a volume ratio of 2:5.

According to one embodiment of the invention, the filtering in the step (iv) may use celite, clay or the like to remove the sticky material after adding the acid.

In the extract of *Cynanchum* sp., the inventors further identify an active ingredient for treatment of arthritis, antofine, in one embodiment of the invention. Thus, the invention further provides a method for treatment of arthritis comprising administrating an effective amount of antofine to a subject in need thereof and a pharmaceutical composition for treatment of arthritis comprising antofine as an active ingredient and a pharmaceutically acceptable carrier in one embodiment.

The antofine according to one embodiment of the invention refers to the phenanthroindolizidine alkaloid as represented in the following Formula (1), enantiomers or salts thereof.

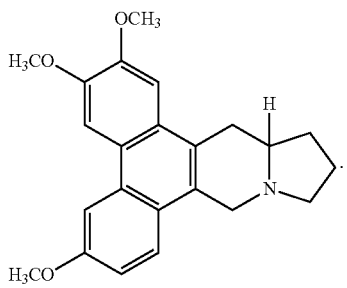

Formula (1)

The enantiomer recited herein includes (+)-antofine and (−)-antofine, but (−)-antofine naturally present as represented in the following Formula (2) is preferable.

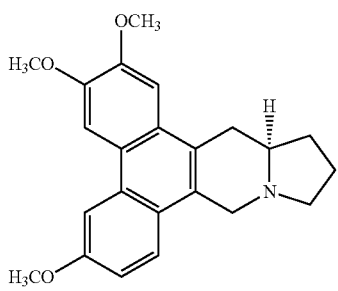

Formula (2)

The salts of antofine recited herein may comprise salts of sodium, potassium, lithium, magnesium, potassium, ammonium, carbonates, nitrates, bicarbonates, hydrochlorides, sulfates, phosphates or silicates. However, the invention is not limited thereto and comprises the salts which do not influence the activity of antofine for the treatment of arthritis.

In one embodiment of the invention, antofine can be obtained from the extraction of the plants, *Albizzia julibrissin, Antitoxicum funebre, Cocculus laurifolius, Cocculus pendulus, Corydalis meifolia, Croton sparsiflours, Cryptocarya oubatchensis, Cryptocarya phyllostemon, Cryptocarya chinensis, Cynanchum hancockianum, Cynanchum inamoenum, Cynanchum komarovi, Cynanchum paniculatum, Cynanchum vincetoxicum, Ficus fistulosa, Ficus septica, Pergularia daemia, Stephania glabra, Tylophora floribunda, Tylophora indica, Tylophora tanakae, Vincetoxicum hirundinaria, Vincetoxicum nigrum, Vincetoxicum officinale, Vincetoxicum pumilu, Vincetoxicum rossicum* or a combination thereof.

The extraction for obtaining antofine may be suitably adjusted depending on the plant species, the tissues for extraction or the like. In one embodiment of the invention, the extraction for obtaining antofine comprises the steps of:

(i) mixing a plant powder with a first solvent to form a first blend;

(ii) heating and filtering the first blend to obtain a first extract;

(iii) concentrating the first extract and substantially adding an acid to form a suspension with a sticky material;

(iv) filtering the suspension to remove the sticky material and obtain a clear solution;

(v) extracting the clear solution with a second solvent to obtain a second extract solution; and (vi) concentrating and purifying the second extract solution.

More specific, the first solvent comprises water, alcohols, esters, ethers, ketones or a combination thereof. The alcohols recited in the first solvent may comprise methanol, ethanol, propanol, isopropanol, butanol, 2-butanol, 2-methylpropanol, 2-methyl-propan-2-ol, 1-pentanol, 2-pentanol, 3-pentanol, 1-hexanol, 2-hexanol, 3-hexanol or a combination thereof. The esters recited in the first solvent may comprise methyl acetate, ethyl acetate, propyl acetate, butyl acetate, pentyl acetate, hexyl acetate or a combination thereof. The ketones recited in the first solvent may comprise acetone, methyl ethyl ketone, 2-pentanone, 3-pentanone or a combination thereof. The ethers recited in the first solvent may comprise ether, propyl ether, isopropyl ether or a combination thereof.

In one example of the invention, the first solvent is a mixture solvent consisting of 80~100% by weight of butyl acetate and 0~20% by weight of ethanol.

In another example of the invention, the first solvent is 50~100% by weight of isopropanol aqueous solution or 90~100% by weight of isopropanol aqueous solution.

According to the invention, the acid added into the first extract is not specifically limited, but hydrochloric acid is preferable. In one example of the invention, 0.1~2N hydrochloric acid is used.

According to one embodiment of the invention, the heating temperature in the step (ii) is from room temperature to boiling temperature of the blend. The heating duration may last 2 hours or more. In one example, the heating temperature is 25~75° C. and 70~75° C. is preferable.

According to one embodiment of the invention, the second solvent may comprise dichloromethane, methanol, ethanol, ether, acetone or a combination thereof, preferably dichloromethane, but it is not limited. The extraction with the second solvent may be preformed at least one time for an increase of the purity. Preferably, the extraction with the second solvent may be performed in one to three times, but not limited thereto.

According to one embodiment of the invention, the purifying in the step (vi) may comprise column chromatography or recrystallization, but it is not limited. The recrystallization may comprise the steps of mixing the concentrated or dried extract with a polar solvent and, after heating and dissolution, cooling down the solution for crystallization. The polar solvent may comprise dichloromethane, methanol, ethanol, ether, acetone or a combination thereof. In one example, dichloromethane is used.

The column chromatography herein refers to a method for separating a component in a mixture by an elute driving the mixture through a column fulfilled with absorbable solid fillers. Because the components in the mixture have different affinities to the fillers of the column and have different solubility to the elute, the components pass through the column with varied velocities and, therefore, are separated. The elute may comprise methanol, ethanol, ethyl acetate, butyl acetate, or a combination thereof. One example of the invention use silica column chromatography with elute consisting of ethyl acetate and methanol in a volume ratio of 2:5.

According to one embodiment of the invention, the filtering in the step (iv) may use celite, clay or the like to remove the sticky material after adding the acid.

Accordingly, one embodiment of the invention provides method for the production of antofine, comprising the steps of:

(i) mixing a plant powder with a first solvent to form a first blend;

(ii) heating and filtering the first blend to obtain a first extract;

(iii) concentrating the first extract and substantially adding an acid to form a suspension with a sticky material;

(iv) filtering the suspension to remove the sticky material and obtain a clear solution;

(v) extracting the clear solution with a second solvent to obtain a second solution; and (vi) concentrating and purifying the second extract solution, wherein the plant is selected from the group consisting of at least one of *Albizzia julibrissin, Antitoxicum funebre, Cocculus laurifolius, Cocculus pendulus, Corydalis meifolia, Croton sparsiflours, Cryptocarya oubatchensis, Cryptocarya phyllostemon, Cryptocarya chinensis, Cynanchum hancockianum, Cynanchum inamoenum, Cynanchum komarovi, Cynanchum paniculatum, Cynanchum vincetoxicum, Ficus fistulosa, Ficus septica, Pergularia daemia, Stephania glabra, Tylophora floribunda, Tylophora indica, Tylophora tanakae, Vincetoxicum hirundinaria, Vincetoxicum nigrum, Vincetoxicum officinale, Vincetoxicum pumilu* and *Vincetoxicum rossicum*.

More specific, the first solvent comprises water, alcohols, esters, ethers, ketones or a combination thereof. The alcohols recited in the first solvent may comprise methanol, ethanol, propanol, isopropanol, butanol, 2-butanol, 2-methylpropanol, 2-methyl-propan-2-ol, 1-pentanol, 2-pentanol, 3-pentanol, 1-hexanol, 2-hexanol, 3-hexanol or a combination thereof. The esters recited in the first solvent may comprise methyl acetate, ethyl acetate, propyl acetate, butyl acetate, pentyl acetate, hexyl acetate or a combination thereof. The ketones recited in the first solvent may comprise acetone, methyl ethyl ketone, 2-pentanone, 3-pentanone or a combination thereof. The ethers recited in the first solvent may comprise ether, propyl ether, isopropyl ether or a combination thereof.

In one example of the invention, the first solvent is a mixture solvent consisting of 80~100% by weight of butyl acetate and 0~20% by weight of ethanol.

In another example of the invention, the first solvent is 50~100% by weight of isopropanol aqueous solution or 90~100% by weight of isopropanol aqueous solution.

According to the invention, the acid added into the first extract is not specifically limited, but hydrochloric acid is preferable. In one example of the invention, 0.1~2N hydrochloric acid is used.

According to one embodiment of the invention, the heating temperature in the step (ii) is from room temperature to boiling temperature of the blend. The heating duration may last 2 hours or more. In one example, the heating temperature is 25~75° C. and 70~75° C. is preferable.

According to one embodiment of the invention, the second solvent may comprise dichloromethane, methanol, ethanol, ether, acetone or a combination thereof, preferably dichloromethane, but it is not limited. The extraction with the second solvent may be preformed at least one time for an increase of the purity. Preferably, the extraction with the second solvent may be performed in one to three times, but not limited thereto.

According to one embodiment of the invention, the purifying in the step (vi) may comprise column chromatography or recrystallization, but it is not limited. The recrystallization may comprise the steps of mixing the concentrated or dried extract with a polar solvent and, after heating and dissolution, cooling down the solution for crystallization. The polar solvent may comprise dichloromethane, methanol, ethanol, ether, acetone or a combination thereof. In one example, dichloromethane is used.

The column chromatography herein refers to a method for separating a component in a mixture by an elute driving the mixture through a column fulfilled with absorbable solid fillers. Because the components in the mixture have different affinities to the fillers of the column and have different solubility to the elute, the components pass through the column with varied velocities and, therefore, are separated. The elute may comprise methanol, ethanol, ethyl acetate, butyl acetate, or a combination thereof. One example of the invention use silica column chromatography with elute consisting of ethyl acetate and methanol in a volume ratio of 2:5.

According to one embodiment of the invention, the filtering in the step (iv) may use celite, clay or the like to remove the sticky material after adding the acid.

In one embodiment, antofine may be obtained from the steps of: mixing powders of *Cynanchum hancockianum* with 50~95% by weight of an ethanol aqueous solution to form a blend; heating the blend to reflux for 2 hours and then filtering out the residues; concentrating the filters and adding 3-times the volume of 0.1~2 N hydrochloric acid; extracting the acidic solution with dichloromethane to obtain a dichloromethane extract; and concentrating and purifying the extract by column chromatography to isolate antofine. For increasing the extraction efficiency, the step of dichloromethane extraction may be repeated twice or more. In one example, the step of dichloromethane extraction is repeated 2~3 times. The concentrated extract may be further recrystalled if needed.

In one example, antofine is produced from the extract of *Cynanchum hancockianum* because containing more amount of antofine and easily available. However, antofine can also be isolated from the plants by the method of extraction as described herein.

According to the method for the production of antofine in one embodiment of the invention, the solvent extraction is able to greatly isolate antofine and reduce the time of repeating the column chromatography. A more than 90% yield of antofine can therefore obtained. Thus, production of antofine according to the invention shows high extraction efficiency and has high industrial applicability.

According to the invention, antofine may not only be obtained from plant extraction but also from chemical syntheses. It has been known that antofine can be chemically synthesized via a proline-catalyzed sequential α-aminoxylation and Horner-Wadsworth-Emmons olefination of aldehyde (Mingbo Cui, et al. Asymmetric synthesis of (R)-antofine and (R)-cryptoleurine via praline-catalyzed sequential α-aminoxylation and Horner-Wadsworth-Emmons olefination of aldehyde. *J. Org. Chem.*, 2010, 75(20), p. 7018~7021).

The effect of the extract of *Cynanchum* sp. and antofine on arthritis can be further determined in animal models. The animal model for arthritis has been established in several studies, such as: the collagen-induced arthritis (CIA) model (Thorbecke G. J., et al., Involvement of endogenous tumor necrosis factor alpha and transforming growth factor beta during induction of collagen type II arthritis in mice. *Proc Natl Acad Sci USA* 89, (1992) 7375~7379.); the adjuvant-induced arthritis model (Barnes D. A., et al., Polyclonal antibody directed against human RANTES ameliorates disease in the Lewis rat adjuvant-induced arthritis model. *J Clin Invest* 101, (1998) 2910~2919.); or the carrageenan-induced paw edema model (Mazzon E., et al., Effect of tumour necrosis factor-α receptor 1 genetic deletion on carrageenan-induced acute inflammation: a comparison with etanercept. *British Society for Immunology, Clinical and Experimental Immunology*, 153(2008):136~149.). The animal model has been broadly used and accepted for estimating the drug efficiency for the treatment of arthritis. The inventors estimated the efficiency of antofine and the extract of *Cynanchum* sp. on the animal models established by the prior arts and tested the effect of antofine and the extract of *Cynanchum* sp. on inhibition of TNF-α and IL-6 in cells to identify that antofine and the extract of *Cynanchum* sp. are potent to be the active ingredients for the treatment of arthritis.

The arthritis according to one embodiment of the invention refers to the disease with joint inflammation and also includes the inflammatory symptoms occurring on tendons, ligaments, bones, cartilages or muscular tissues. The arthritis recited herein may comprise infectious arthritis, rheumatoid arthritis, juvenile idiopathic arthritis, systemic lupus erythematosus, osteoarthritis, fibromyalgia, scleroderma, spondyloarthropathies, gout, polymyalgia rheumatic, polymyositis, psoriatic arthritis, bursitis or tendinitis. The subject herein may comprise mammals, such as mice, rats, cats, dogs, goats, rabbits, cows, monkeys, gorilla, chimpanzees or human beings.

The pharmaceutically acceptable carrier recited herein refers to pharmaceutically acceptable additives which do not change the activity of the active ingredient, such as excipients, anti-oxidants, emulsifiers, dispersions, septic agents, flavors, pigments, buffers, solvents, pH adjusting agents, surfactants, or the like. The pharmaceutical composition according to one embodiment of the invention may be formulated into a dosage form, such as pellets, capsules, film-coated tablets, blowing agents, granules, powders, suspensions, syrups, or the like, for administration and storage. In addition, the pharmaceutical composition in one embodiment of the invention may be administered individually or co-administrated with other agents.

Another embodiment of the invention also provides a dietary supplement comprising antofine or the extract of *Cynanchum* sp. as active ingredients for dietary supplements. The dietary supplement recited herein may be directly eaten or drunk. Alternatively, the dietary supplement may be added in food, such as beverages, soups or the like, for eating.

The dietary supplement recited herein may comprise food additives, such as anti-oxidants, preservatives, leavening agents, flavors, edible pigments, thickeners, solidifiers, dispersions, excipients, or the like, if desirable. The dietary supplement recited herein may be formulated into granules, pellets, tablets, capsules or powders, or added into beverages or syrups for eating and storage.

Example 1

Isolation of Antofine 1 kg of powder of *Cynanchum hancockianum* was added into a 22 L-three necked flask. A 95% ethanol aqueous solution 10 L was then added. The flask was heated to reflux and maintained at a temperature for 2 hours. The filter was collected for the next steps. The same heating step was repeated for the residue once and the filter was collected and mixed with the filter obtained above. The mixture was concentrated to 1/20 of total volume by a rotary evaporator (EYELA, Type N-1000). Three-times the volume of the 0.5N HCl aqueous solution was added then to form sticky materials. The sticky material was filtered out by Celite® 545 and collected the clear solution. The same volume of $CH_2Cl_2$ was added and the solution was extracted three times. The $CH_2Cl_2$ fraction was collected and concentrated to become thicker. A minor of Silica Gel 60 (Merck) was then added and mixed uniformly. The mixture was then added into a column filled with Silica Gel 60 (Merck) and eluted by ethyl acetate and methanol (EA:MeOH=2:5). The filter was recrystallized with $CH_2Cl_2$. A pale yellow crystal 400 mg was obtained.

Figure 2:
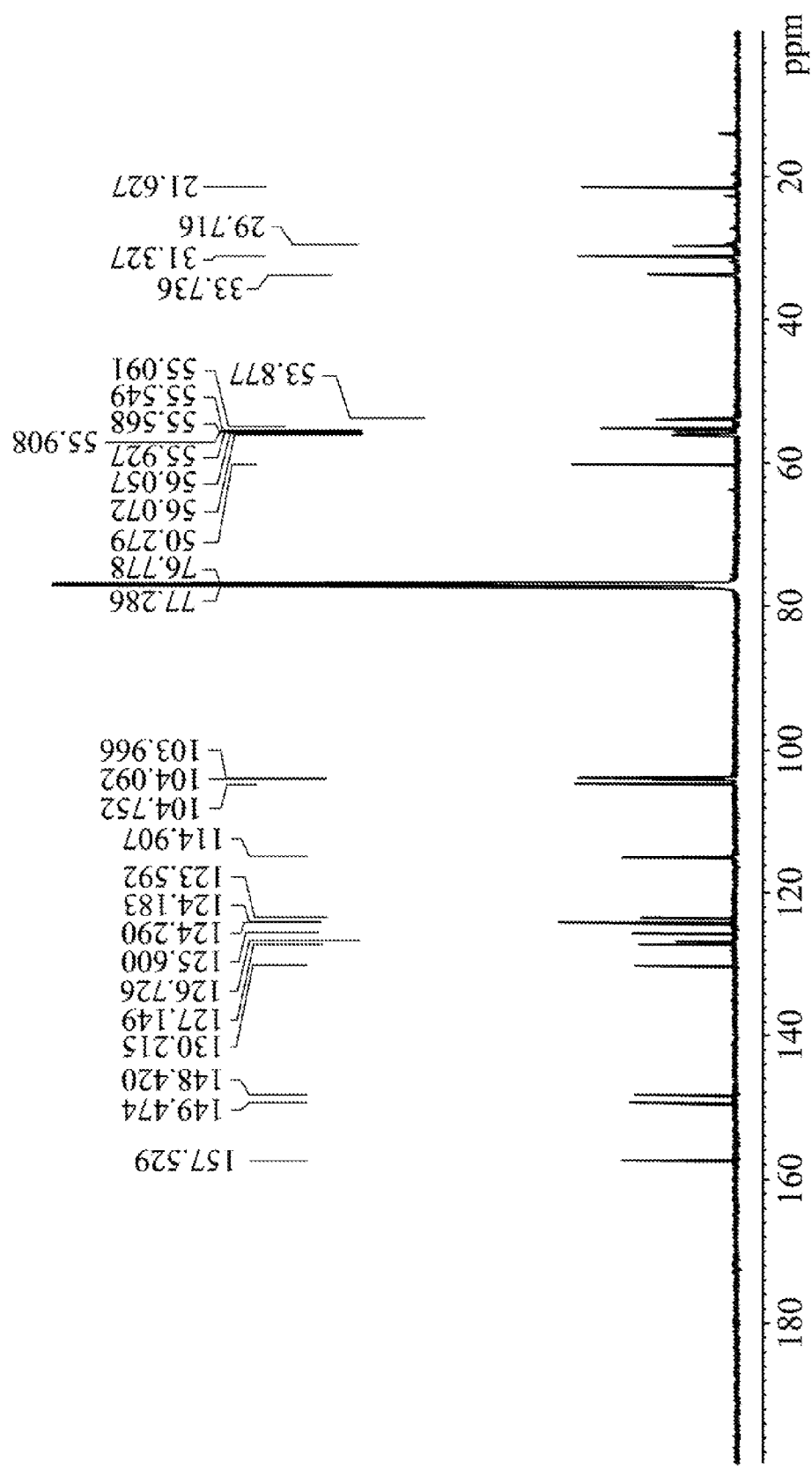

The pale yellow crystal was then analyzed by $^1H$ NMR and $^{13}C$ NMR spectroscopy (FIGS. 1 and 2).

$^1H$ NMR (500 MHz, $CDCl_3$) δ 1.83 (m, 1H), δ1.96 (m, 1H), δ2.09 (m, 1H), δ 2.29 (m, 1H), δ2.50 (td, 1H), δ2.54 (m, 1H), δ2.95 (dm, 1H), δ63.40 (m, 1H), δ63.51 (q, 1H), δ 3.75 (d, 1H), δ4.06 (s, 1H), δ4.10 (s, 1H), δ4.15 (s, 1H), δ4.74 (d, 1H), δ7.25 (dd, 1H), δ 7.36 (s, 1H), δ7.86 (d, 1H), δ7.95 (d, 1H), δ7.96 (s, 1H).

$^{13}C$ NMR (500 MHz, $CDCl_3$) δ21.63, 31.33, 33.74, 53.88, 55.09, 55.56, 55.92, 56.06, 60.28, 103.97, 104.09, 104.75, 114.91, 123.59, 124.18, 124.29, 125.60, 126.73, 127.15, 130.22, 148.42, 149.47, 157.53.

MS (EI) (m/z) 363.

($[M+H]^+$) 364.1912.

The crystal was identified as (−)-antofine with a molecular weight of 363.45 and molecular formula $C_{23}H_{25}NO_3$ as represented in the following formula.

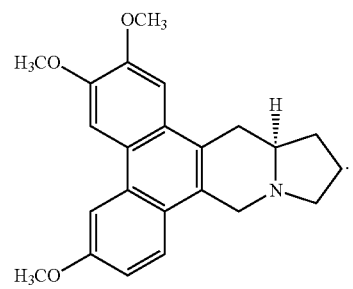 [SMILES: COc1ccc2c3c(c4cc(OC)c(OC)cc4c2c1)C[C@H]1CCCN1C3]

Example 2

Effect of Ethanol Extracts of *Cynanchum* sp. on TNF-α Inhibition

Ethanol Extract of *Cynanchum hancockianum*

0.5 g of powder of *Cynanchum hancockianum* was added into 95% of an ethanol aqueous solution 25 ml. The ethanol mixture was shaken overnight at room temperature. After drying and being concentrated, the ethanol extract was obtained. The ethanol extract was then diluted with 0.4% DMSO to form 19 μg/ml, 56 μg/ml, 167 μg/ml and 500 μg/ml of ethanol extracts of *Cynanchum hancockianum*, respectively. The extracts were kept for the next step.

U937 Cell Line

A human myeloid leukemia cell line U937 (Rockville, Md.) was obtained from ATCC. The cell line was cultured in a RPMI 1640 medium with a 10% fetal calf serum (FCS) at 37° C., 5% $CO_2$. The cell line maintained in exponential growth. For inducing differentiation, the cells with a starting concentration of $4 \times 10^5$ cell/ml were cultured in T150 containing 50 ng/ml PMA (Sigma) for 24 hours. Subsequently, the cells were moved to a fresh medium without PMA and cultured for 48 hours. The cells were collected with rubber policeman (Bellco Glass, Vineland, N.J.) gently scraping the medium bottle for the next step.

TNF-α Inhibition

Figure 3:
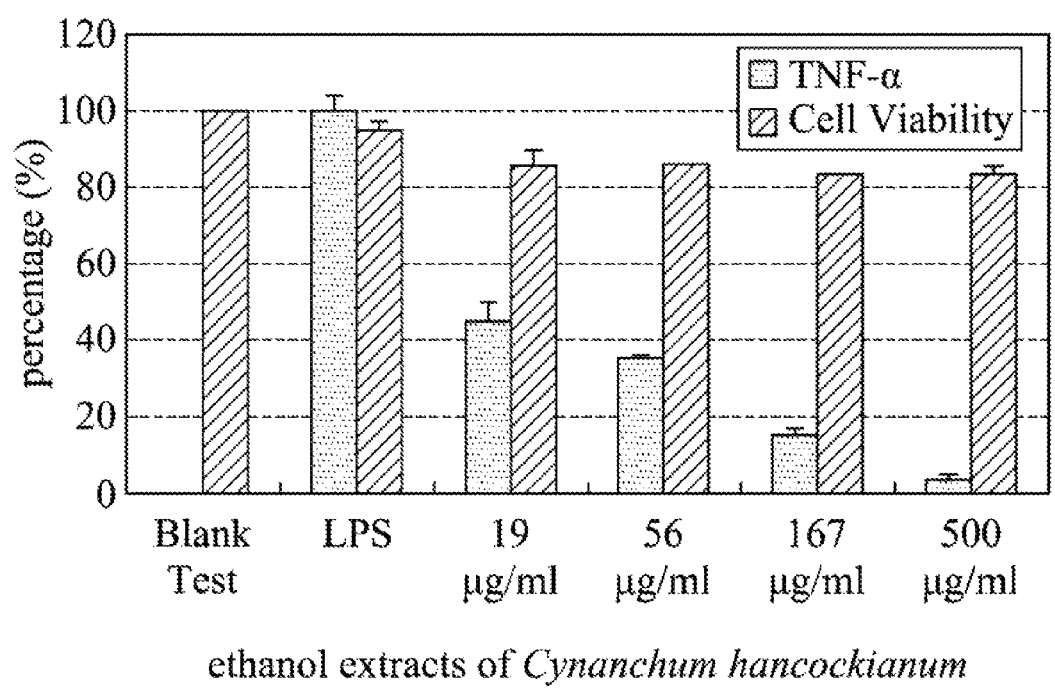
FIG. 3 is the effect of the ethanol extract of _Cynanchum hancockianum_ on TNF-$\alpha$ inhibition and cell viability in a U937 cell line according to one embodiment.

The activated U937 cells were seeded into a 96-well plate to form a concentration of $1.6 \times 10^5$ cell/well. The ethanol extracts of *Cynanchum hancockianum* in different concentrations were respectively added 10 μl to the 96-well plate. The final volume of each well was 190 μl. The plate was cultured at 37° C., 5% $CO_2$ for 30 min. Then each well was added 2 μg/ml of lipopolysaccharide (LPS) in PBS 10 μl and cultured at 37° C. for 4 hours. The supernate was collected by Analyses Kit (R&D System, Minneapolis, Minn.). The amount of TNF-α was analyzed by an ELISA (TNF-α duoset, R&D, Minneapolis, Minn.). Cell viability was tested by MTT (3-(4,5-dimethyl-thiazol-2-yl)2,5-diphenyltrazolium, Sigma). The blank test without adding the ethanol extract of *Cynanchum hancockianum* and LPS was set. The result is shown in Table 1 and FIG. 3. $IC_{50}$ was 17 μg/ml.

TABLE 1

|  | TNF-α (%) | Cell viability (%) |
|---|---|---|
| Blank test | 0 | 100 |
| LPS (no ethanol extract was added) | 100 | 95 |
| Ethanol Extracts 19 μg/ml | 45 | 86 |
| 56 μg/ml | 35 | 86 |
| 167 μg/ml | 15 | 83 |
| 500 μg/ml | 4 | 83 |

Example 3

Effect of Antofine on TNF-α Inhibition

Figure 4:
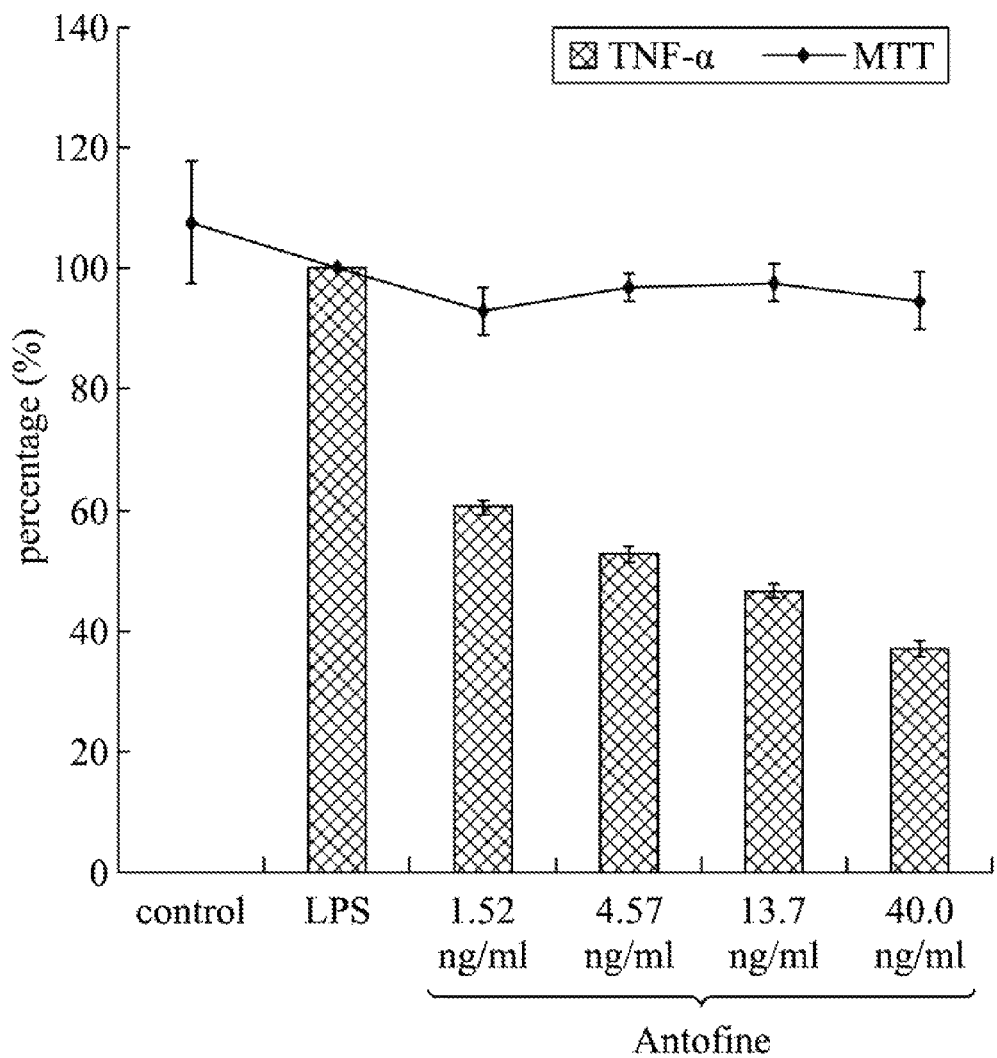
FIG. 4 is the effect of antofine on TNF-$\alpha$ inhibition and cell viability in a U937 cell line according to one embodiment.

The activated U937 cells obtained from Example 2 were seeded into a 96-well plate to form a concentration of $1.6 \times 10^5$ cell/well. Antofine isolated from Example 1 was diluted with 0.4% DMSO to become 1.52 ng/ml, 4.57 ng/ml, 13.7 ng/ml and 40.0 ng/ml and 10 μl of each was added into the plate. The final volume of each well was 190 μl. The plate was cultured at 37° C., 5% $CO_2$ for 30 min. Then each well was added 2 μg/ml of lipopolysaccharide (LPS) in PBS 10 μl and cultured at 37° C. for 4 hours. The supernate was collected by Analyses Kit (R&D System, Minneapolis, Minn.). The amount of TNF-α was analyzed by an ELISA and cell viability was tested by MTT. The result is shown in FIG. 4. $IC_{50}$ was 7 ng/ml.

Example 4

Effect of Extracts of *Cynanchum* sp. on TNF-α and IL-6 Inhibition in an LPS-Induced Model Extracts of *Cynanchum* sp.

1.2 kg of powder of *Cynanchum atratum* was added to 6.0 L of a 50% ethanol aqueous solution and shaken at room temperature overnight. After drying and being concentrated, the extract of *Cynanchum atratum* 137 g was obtained.

LPS-Induced Mice Model

Figure 5:
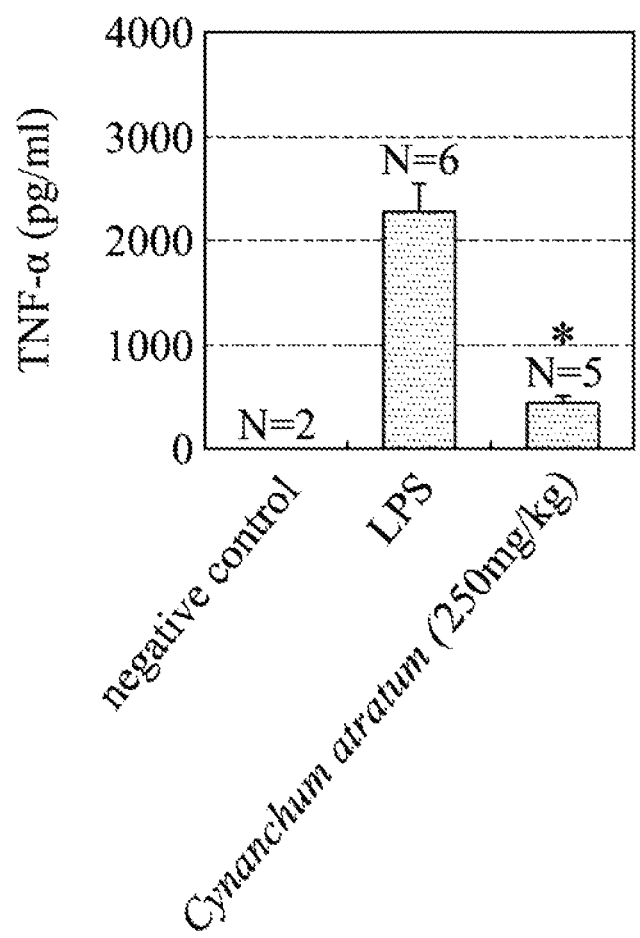
FIG. 5 is the effect of extracts of _Cynanchum_ sp. on TNF-$\alpha$ inhibition in an LPS-induced model according to one embodiment.
Figure 6:
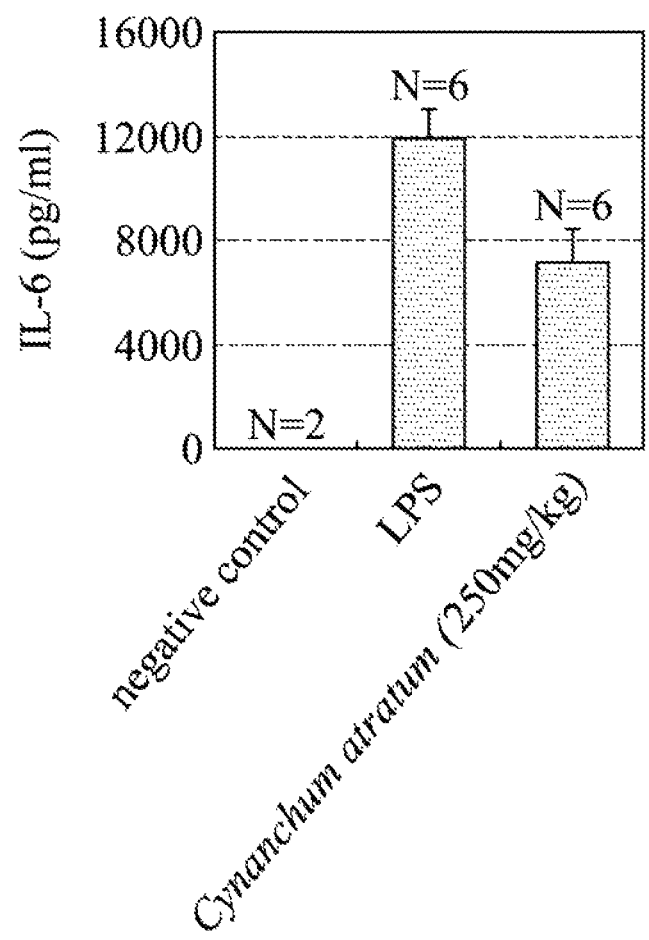
FIG. 6 is the effect of extracts of _Cynanchum_ sp. on IL-6 inhibition in an LPS-induced model according to one embodiment.

Six male BALB/c mice were grouped and fed the extract of *Cynanchum atratum* 250 mg/kg and a carrier (5% ethanol in 30% Cremophore EL (CrEL) (BASF)). One group of the mice which was fed the carrier without the extract was set as a control group. After 2 hours, the mice were i.p. injected with 1 mg/kg of LPS. The blood was collected 1.5 hours after the injection. The amounts of TNF-α and IL-6 in the blood were analyzed with an ELISA (R&D Systems). The results are shown in Table 2 and FIGS. 5 and 6.

TABLE 2

|  | TNF-α | | IL-6 | |
|---|---|---|---|---|
|  | Average (pg/ml) | Inhibition (%) | Average (pg/ml) | Inhibition (%) |
| Negative control | 0 | 0 | 0 | 0 |
| LPS (5% ethanol in 30% CrEL) | 2269 | — | 11916 | — |
| Extract of *Cynanchum atratum* | 414* | 81.76 | 7149* | 40.0 |

*$p < 0.05$

Example 5

Effect of Extracts of *Cynanchum* sp. on TNF-α and IL-6 Inhibition in an LPS-Induced Model Extracts of *Cynanchum* sp.

1.2 kg of powders of *Cynanchum atratum* (tailings), *Cynanchum stauntoni*, *Cynanchum paniculatum*, and *Cynanchum atratum* (erects) was respectively added to 6.0 L of a 50% ethanol aqueous solution and shaken at room temperature overnight. After drying and being concentrated, the extracts of each *Cynanchum* sp. were obtained.

LPS-Induced Mice Model

Figure 7:
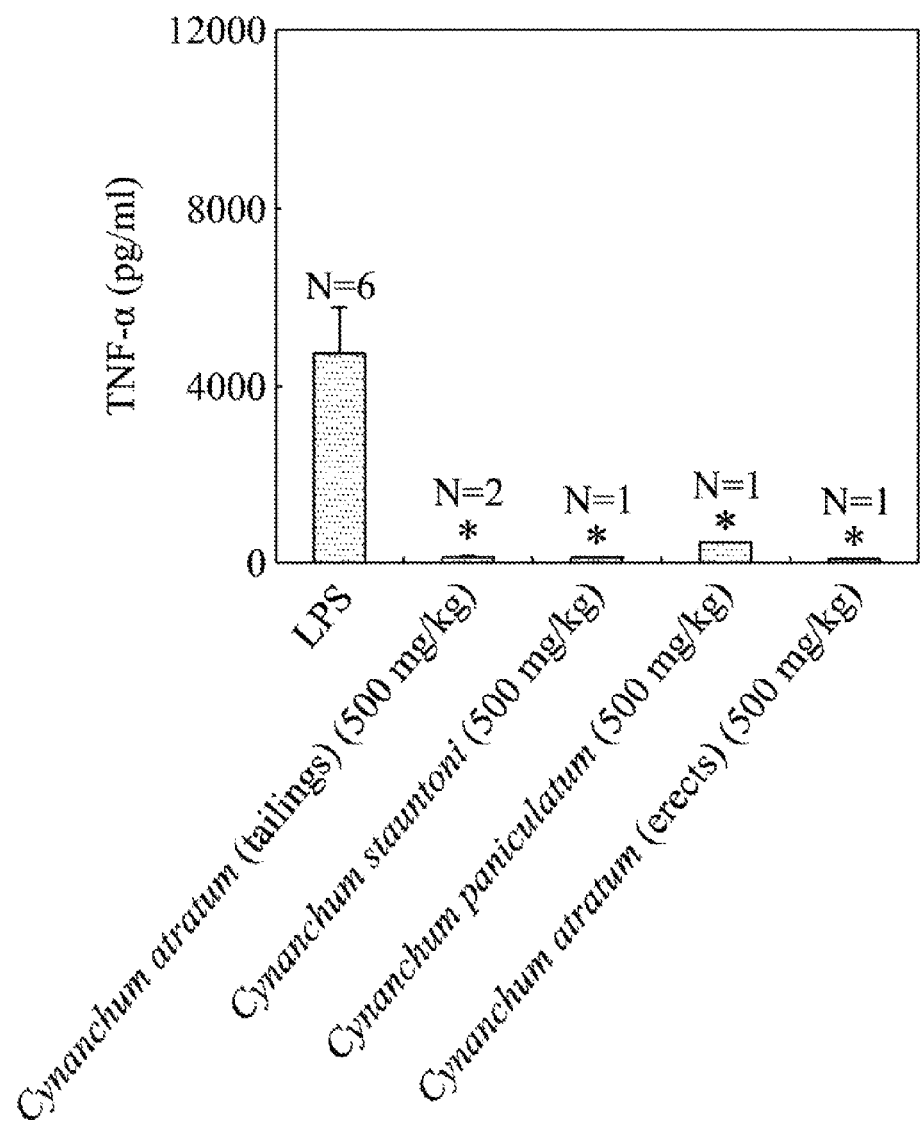
FIG. 7 is the effect of several extracts of _Cynanchum_ sp. on TNF-$\alpha$ inhibition in an LPS-induced model according to one embodiment.
Figure 8:
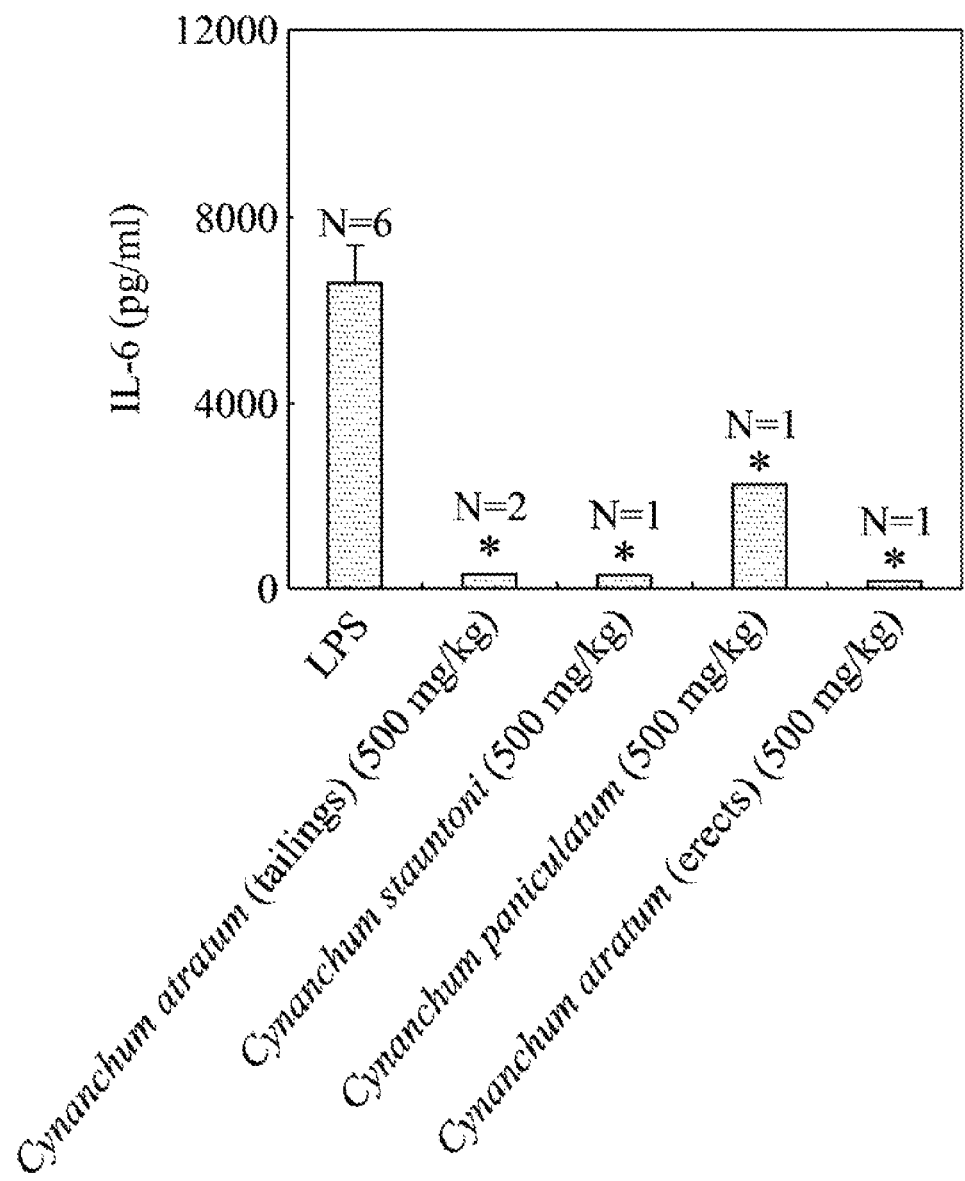
FIG. 8 is the effect of several extracts of _Cynanchum_ sp. on IL-6 inhibition in an LPS-induced model according to one embodiment.

Four male BALB/c mice were grouped and fed the extracts of *Cynanchum* sp. 500 mg/kg each and a carrier (5% ethanol in 30% CrEL (BASF)). A group fed with the carrier without the extracts was set as a control group. After 2 hours, the mice were i.p. injected with 1 mg/kg of LPS. The blood was collected 1.5 hours after the injection. The amounts of TNF-α and IL-6 in the blood were analyzed with an ELISA (R&D Systems). The results are shown in Table 3 and FIGS. 7 and 8.

TABLE 3

|  | TNF-α | | IL-6 | |
|---|---|---|---|---|
|  | Average (pg/ml) | Inhibition (%) | Average (pg/ml) | Inhibition (%) |
| Control | 4743 | — | 6577 | — |
| Extract of *Cynanchum atratum* (tailing) | 137* | 97.1 | 269* | 95.9 |
| Extract of *Cynanchum stauntoni* | 118* | 97.5 | 263* | 96.0 |
| Extract of *Cynanchum paniculatum* | 485* | 89.8 | 2199* | 66.6 |
| Extract of *Cynanchum atratum* (erect) | 99* | 97.9 | 137* | 97.9 |

*$p < 0.05$

Example 6

Effect of Extracts of *Cynanchum* sp. on TNF-α and IL-6 Inhibition in an LPS-Induced Model Extracts of *Cynanchum* sp.

Powders of *Cynanchum hancockianum* and *Cynanchum atratum* 50 g each were added to 500 ml of a 40% ethanol aqueous solution and heated to reflux for 1 hour. After drying and being concentrated, the extracts were obtained in a concentration of 15±2 g, and 25±2% of solid contents, respectively.

LPS-Induced Mice Model

Figure 9:
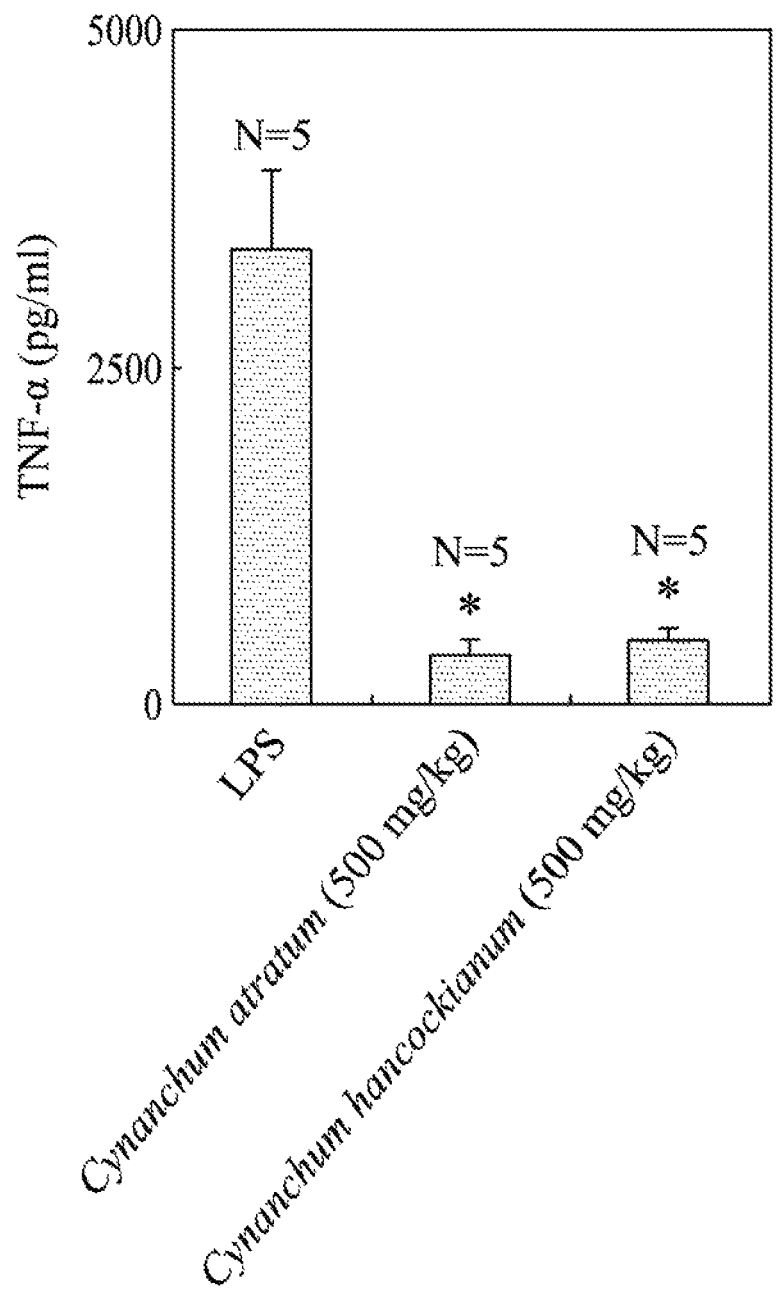
FIG. 9 is the effect of several extracts of _Cynanchum_ sp. on TNF-$\alpha$ inhibition in an LPS-induced model according to one embodiment.
Figure 10:
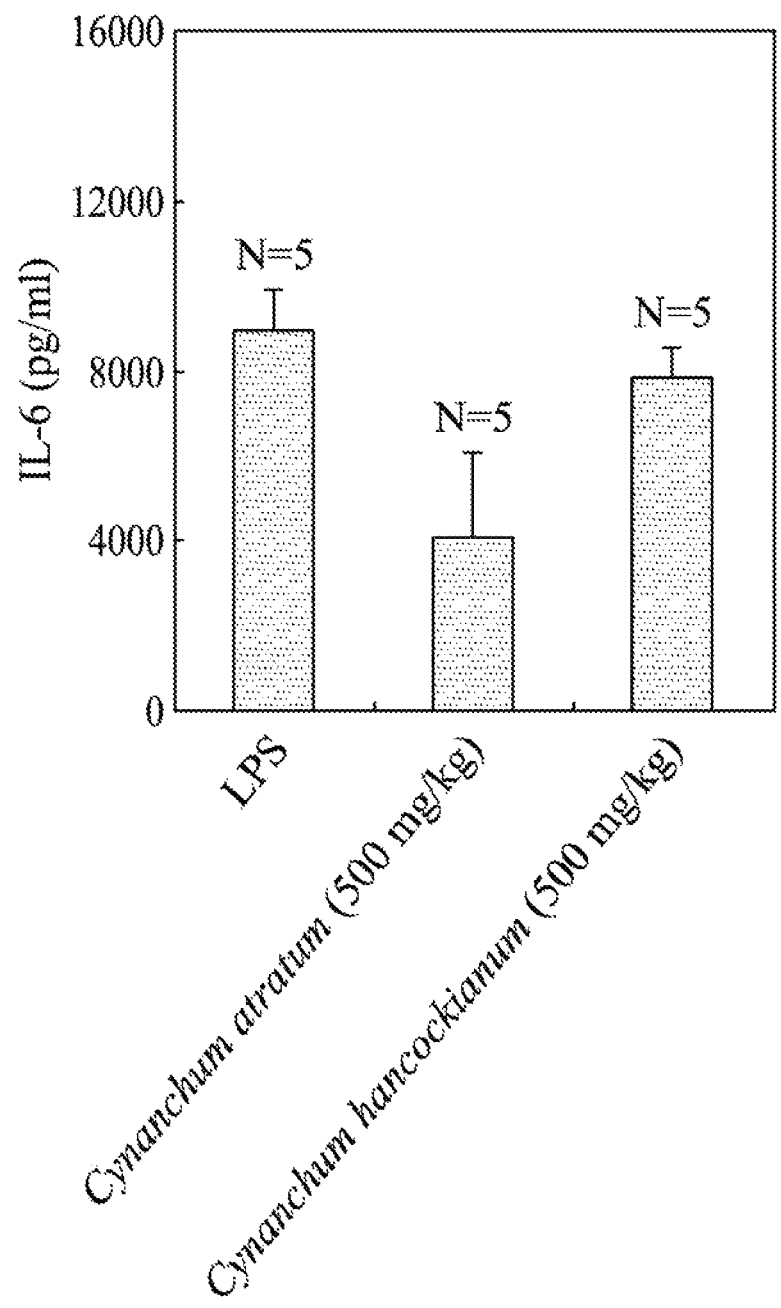
FIG. 10 is the effect of several extracts of _Cynanchum_ sp. on IL-6 inhibition in an LPS-induced model according to one embodiment.

Five male BALB/c mice were grouped and fed the extracts of *Cynanchum* sp. 500 mg/kg each and a carrier (5% ethanol in 30% CrEL (BASF)). A group fed with the carrier without the extracts was set as a control group. After 2 hours, the mice were i.p. injected with 1 mg/kg of LPS. The blood was collected 1.5 hours after the injection. The amounts of TNF-α and IL-6 in the blood were analyzed with an ELISA (R&D Systems). The results are shown in Table 4 and FIGS. 9 and 10.

TABLE 4

|  | TNF-α | | IL-6 | |
| --- | --- | --- | --- | --- |
|  | Average (pg/ml) | Inhibition (%) | Average (pg/ml) | Inhibition (%) |
| Control | 3377 | — | 8956 | — |
| Extract of *Cynanchum atratum* | 364* | 89.2 | 4016 | 55.2 |
| Extract of *Cynanchum hancockianum* | 470* | 86.1 | 7764 | 13 |

*p < 0.05

Example 7

Effect of 50% Ethanol Extract of *Cynanchum Atratum* on the Paw Edema in a Carrageenan-Induced Rat Model Five Long-Evan rats were set in a group. The ankle of the left hindpaw of each rat was measured as the basis of the hindpaw volume at the beginning of the test. The experimental groups were fed 250 mg/kg, 500 mg/kg and 1000 mg/kg of *Cynanchum atratum*, respectively. The carrier control group was fed 1% CMC (carboxymethyl cellulose). The positive control group was fed 3 mg/kg indomethacin. After 1 hour, 1% carrageenan-saline 0.1 ml was injected into the left hindpaw of all rats. The volume of the left hindpaw was measured by a plethysmometer (PV-01, DR instrument, Taiwan) at hours 0, 1, 2 and 3 after carrageenan injection.

The inhibition was calculated by the following formula:

$$\text{Inhibition }(\%) = (Nt - Nv)/Nv \times 100$$

Nt: Net change of the left paw volume of the experimental group.
Nv: Net change of the left paw volume of the carrier control.

Figure 11:
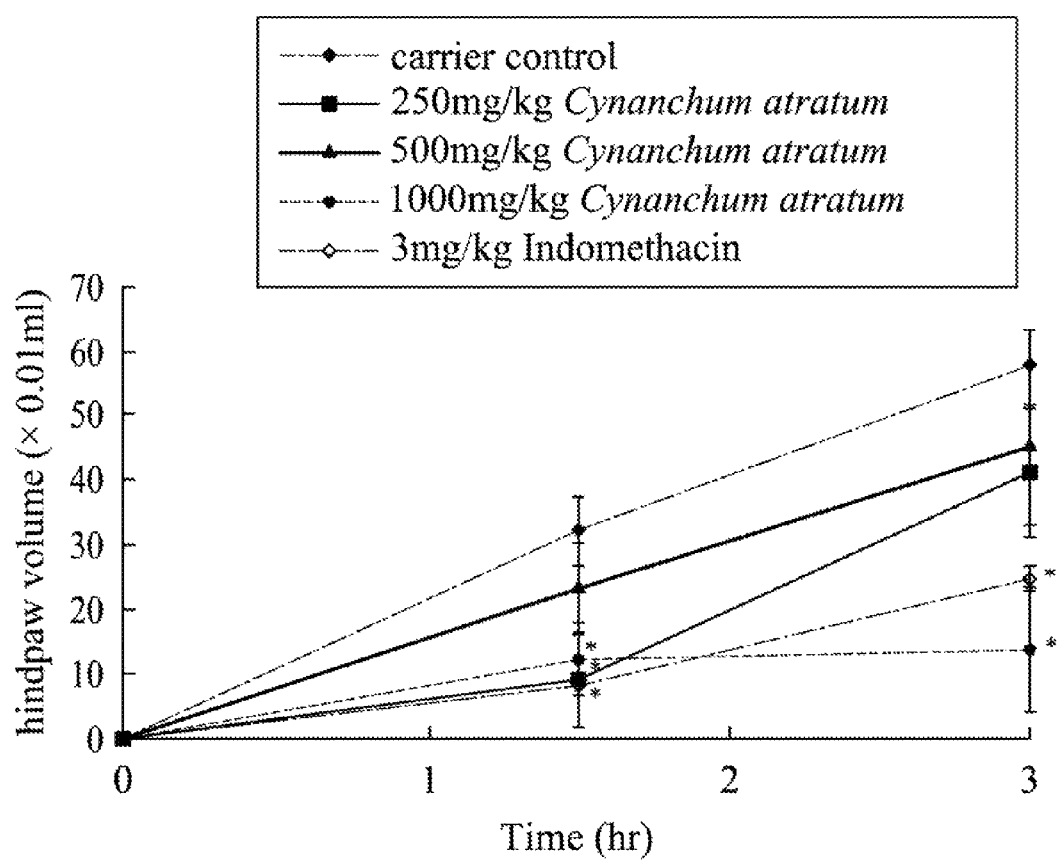
FIG. 11 is the effect of extracts of _Cynanchum_ sp. on the hindpaw volume in a carrageenan-induced rat model according to one embodiment.

As the inhibition was negative, it indicated that the administration had anti-inflammatory effects. The results are shown in FIG. 11.

Example 8

Effect of 50% Ethanol Extracts of *Cynanchum atratum* in an Adjuvant-Induced Arthritis Model The ankles of each Lewis rat were measured as the basis of a hindpaw volume at the beginning of the test. 20 mg/ml of *Mycobacterium butyricum* suspended in squalene 50 μl was injected subdermally to three points near the basis of the tail. From the day of the injection, the experimental group was fed 100 mg/kg and 200 mg/kg of *Cynanchum atratum* per day, the carrier control group was fed 5% of ethanol and 0.025% of Tween 20 in 1% CMC per day and the positive control group was fed 3 mg/kg indomethacin per day until the study was finished. The symptoms of the arthritis in each group were estimated according to the following scores:

0: The foot was not red and swelling;
1: The foot was slightly red and swelling or one toe joint was red and swelling;
2: The foot was apparently red and swelling or more than two toe joints were red and swelling;
3: The hindpaw was incapable of function for walking;
4: The ankle joint was incapable of moving.

Figure 12:
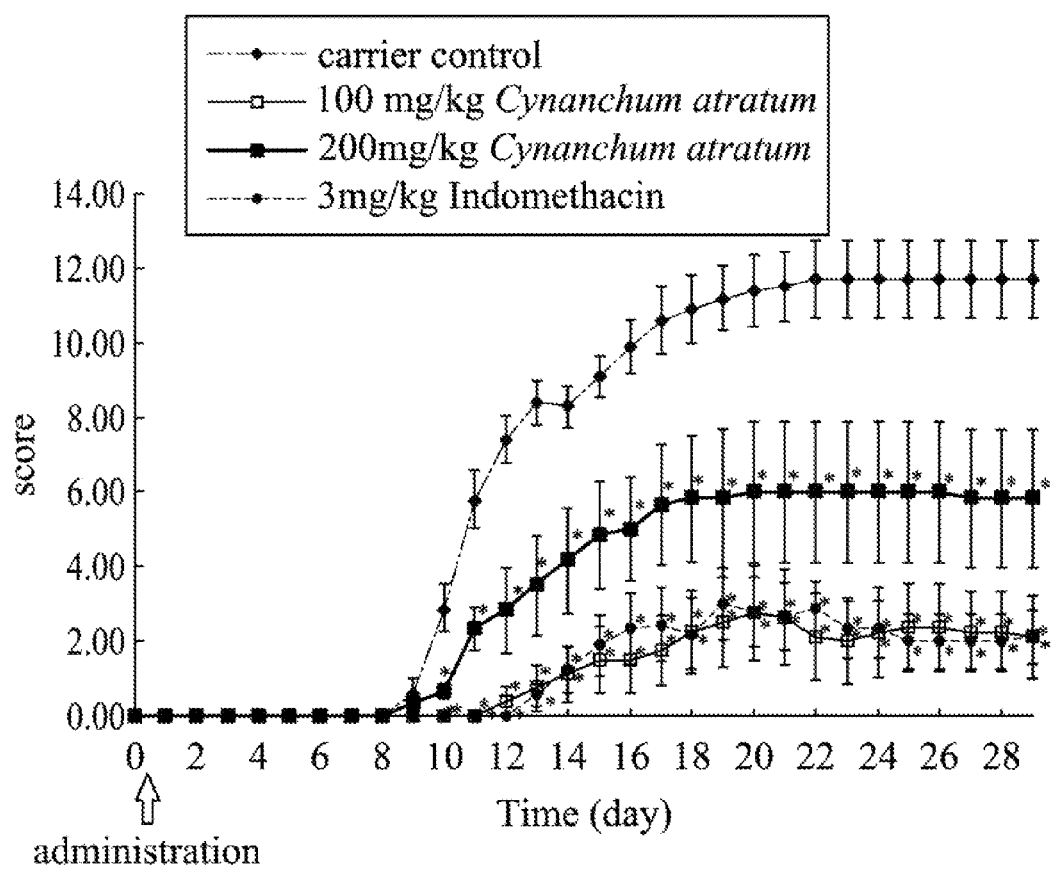
FIG. 12 is the effect of extracts of _Cynanchum_ sp. on the arthritis scores in an adjuvant-induced arthritis model according to one embodiment.

The hindpaw volume was measured by a plethysmometer and shown as a percentage of the average weight of each rat. The accuracy of the weight measurement was more than 0.1 g (METTLER TOLDEO, PB1501). The result is shown in FIG. 12. * represents p<0.05, which shows statistically significant differences.

Example 9

Effect of *Cynanchum Atratum* Extract on Anti-Inflammation in an Adjuvant-Induced Arthritis Model The ankles of each Lewis rats were measured as the basis of a hindpaw volume at the beginning of the test. 20 mg/ml of *Mycobacterium butyricum* suspended in squalene 50 μl was injected subdermally to three points near the basis of the tail. From the day of the injection, the experimental group was fed 16.7 mg/kg and 50 mg/kg of *Cynanchum atratum* extracts (50% ethanol extracts obtained from Example 5) and 50 mg/kg and 100 mg/kg of *Cynanchum atratum* extracts (95% ethanol extracts) per day, and the carrier control group was fed 5% of ethanol and 0.025% of Tween 20 in 1% CMC per day until the study was finished. A negative control was set. The symptoms of the arthritis in each group were estimated according to the scores:

0: The foot was not red and swelling;
1: The foot was slightly red and swelling or one toe joint was red and swelling;
2: The foot was apparently red and swelling or more than two toe joints were red and swelling;
3: The hindpaw was incapable of function for walking;
4: The ankle joint was incapable of moving.

Figure 13:
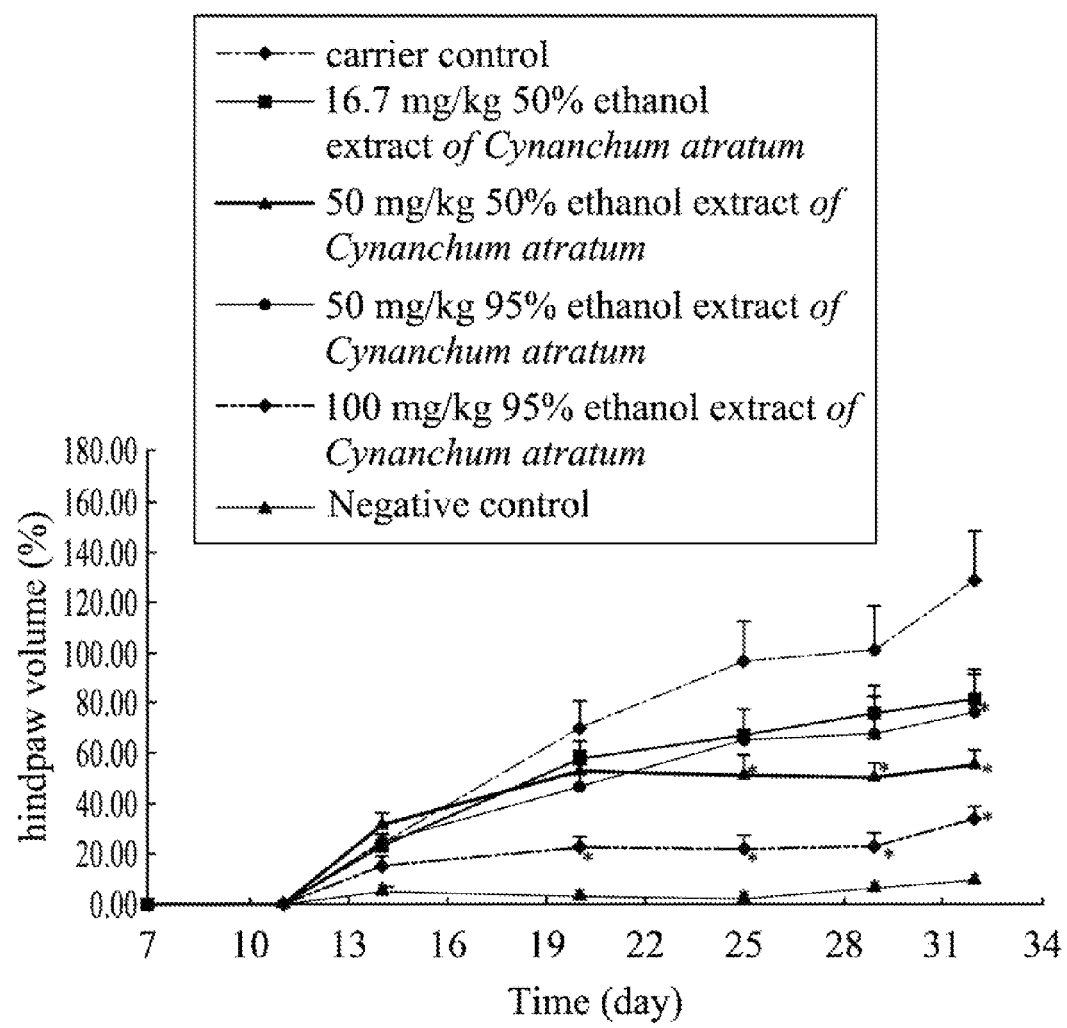
FIG. 13 is the effect of extracts of *Cynanchum* sp. on the hindpaw volume in an adjuvant-induced arthritis model according to one embodiment.

The hindpaw volume was measured by a plethysmometer and shown as a percentage of the average weight of each rat. The accuracy of weight measurement was more than 0.1 g (METTLER TOLDEO, PB1501). The result is shown in FIG. 13. * represents p<0.05, which shows statistically significant differences.

Example 10

Effect of Antofine Administration Regime in a Collagen-Induced Arthritis Model

50 μg of a fetus bovine type II collagen (CII, Chondrex) was emulsified in a complete Freund's adjuvant (CFA, Sigma). The ankle volume was measured as the basis of a hindpaw volume. On the eighth day after the primary immune, each rat was injected with 100 μg of the collagen emulsified in IFA (Sigma) to induce arthritis. The carrier control group was i.p. injected with 2 ml/kg of 0.5% CMC rats every two days until day 21. The experimental group was fed antofine isolated from Example 1 according to the following regimes:

Group 1 was i.p. injected with 3 mg/kg of antofine every two days until Day 20 and then i.p. injected with 3 mg/kg of antofine per day on Day 21~23;

Group 2 was i.p. injected with 3 mg/kg of antofine every three days until Day 20 and then i.p. injected with 3 mg/kg of antofine per day on Day 21~23;

Group 3 was i.p. injected with 2 mg/kg of antofine every two days until Day 20 and then i.p. injected with 3 mg/kg of antofine per day on Day 21~23;

Group 4 was i.p. injected with 3 mg/kg of antofine per day for 5 days, and then stop administration on the next nine days, and i.p. injected with 3 mg/kg of antofine per day on Day 21~23.; and the positive control group was fed 3 mg/kg Indomethacin per day.

All rats were scarified on Day 24.

Figure 14:
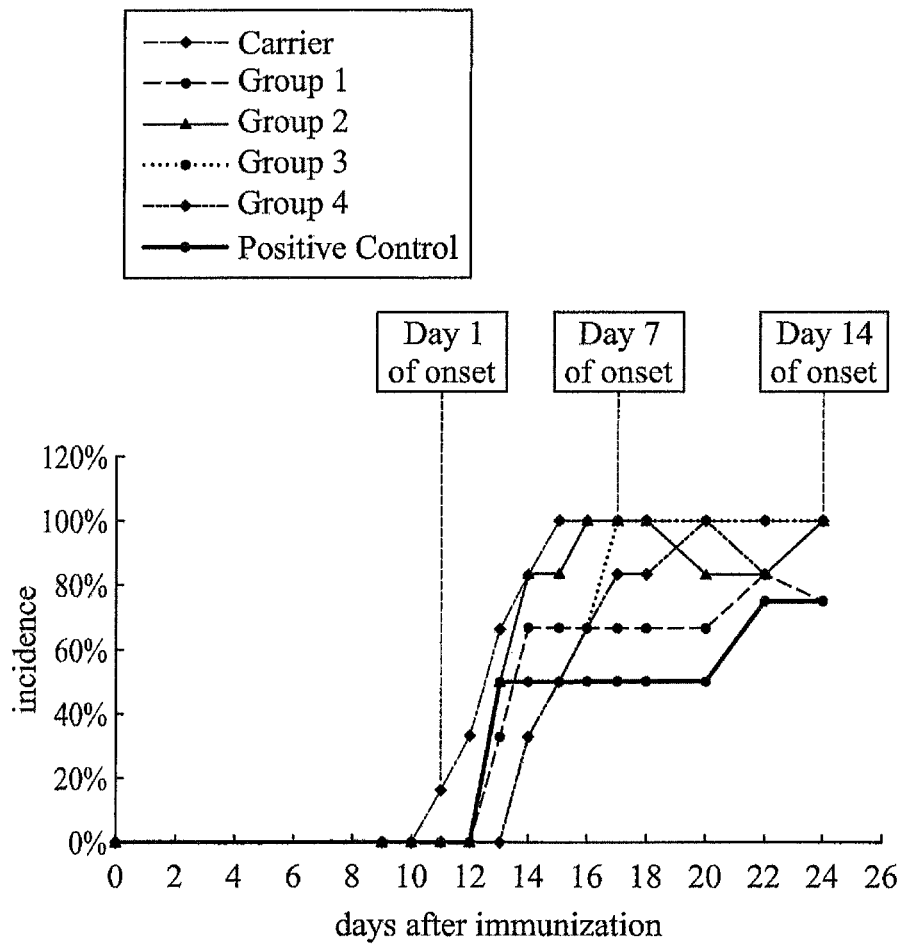
FIG. 14 is the effect of antofine regimes on arthritis incidence in a collagen-induced arthritis model according to one embodiment.
Figure 15:
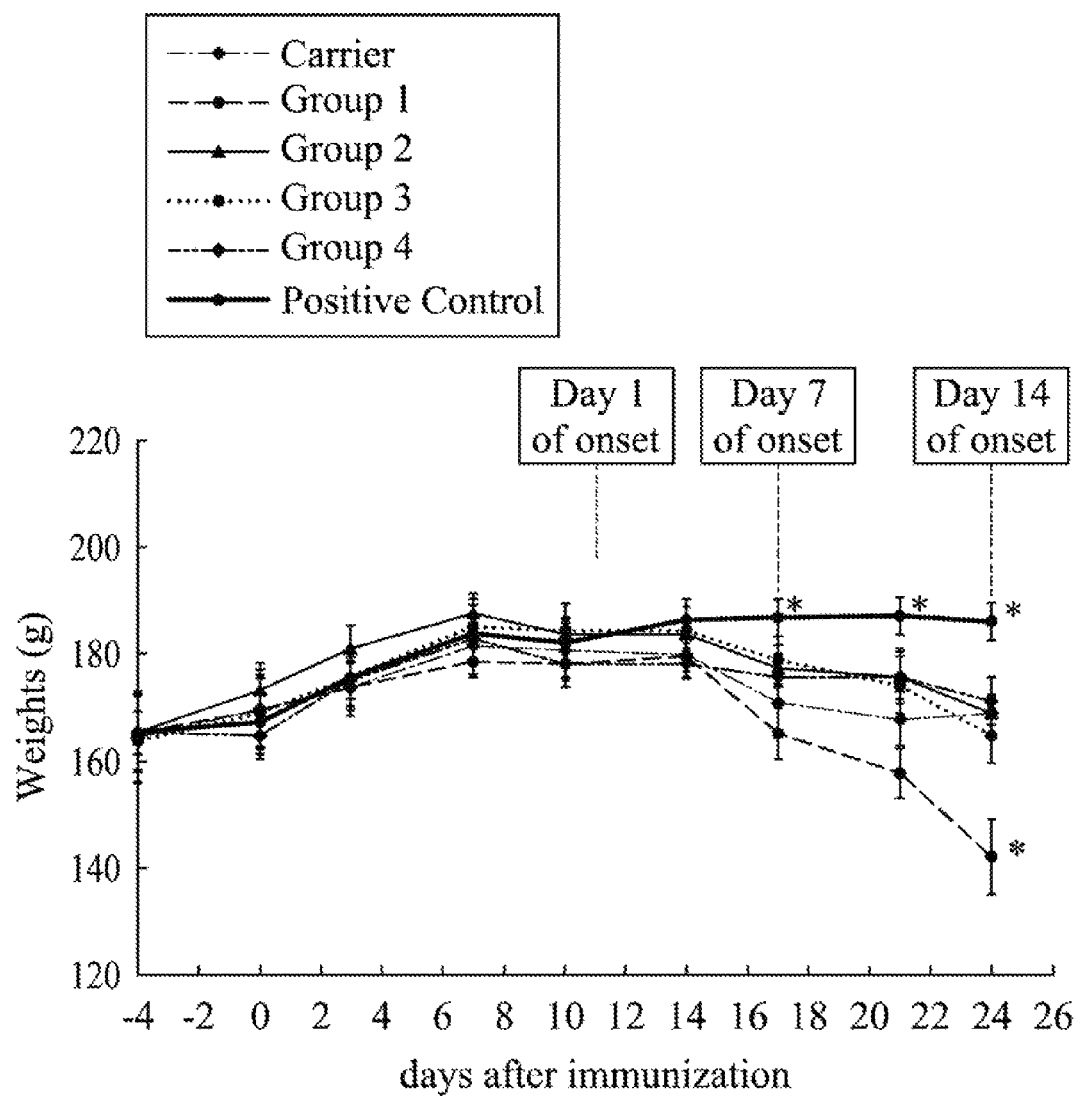
FIG. 15 is the effect of antofine regimes on weight changes in a collagen-induced arthritis model according to one embodiment.

Morbidities of each group are shown in FIG. 14. Weight changes are shown in FIG. 15. The results revealed that Group 1 and Group 4 showed decreased morbidities and delayed onsets but weights were not greatly changed under the treatment of various doses of antofine and the regimes.

The symptoms of the arthritis in each group were estimated according to the scores:

0: The foot was not red and swelling;

1: The foot was slightly red and swelling or one toe joint was red and swelling;

2: The foot was apparently red and swelling or more than two toe joints were red and swelling;

3: The hindpaw was incapable of function for walking;

4: The ankle joint was incapable of moving.

Figure 16:
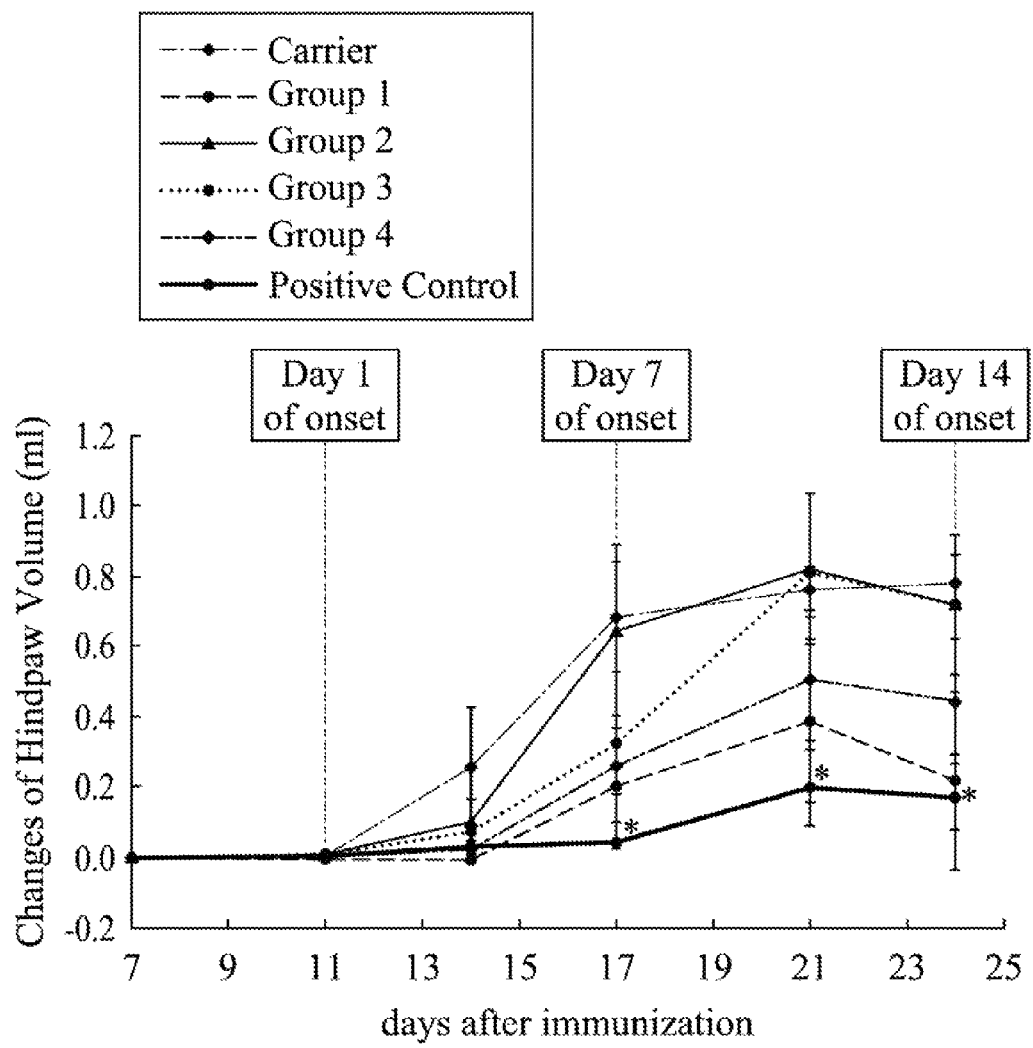
FIG. 16 is the effect of antofine regimes on the hindpaw volume in a collagen-induced arthritis model according to one embodiment.
Figure 17:
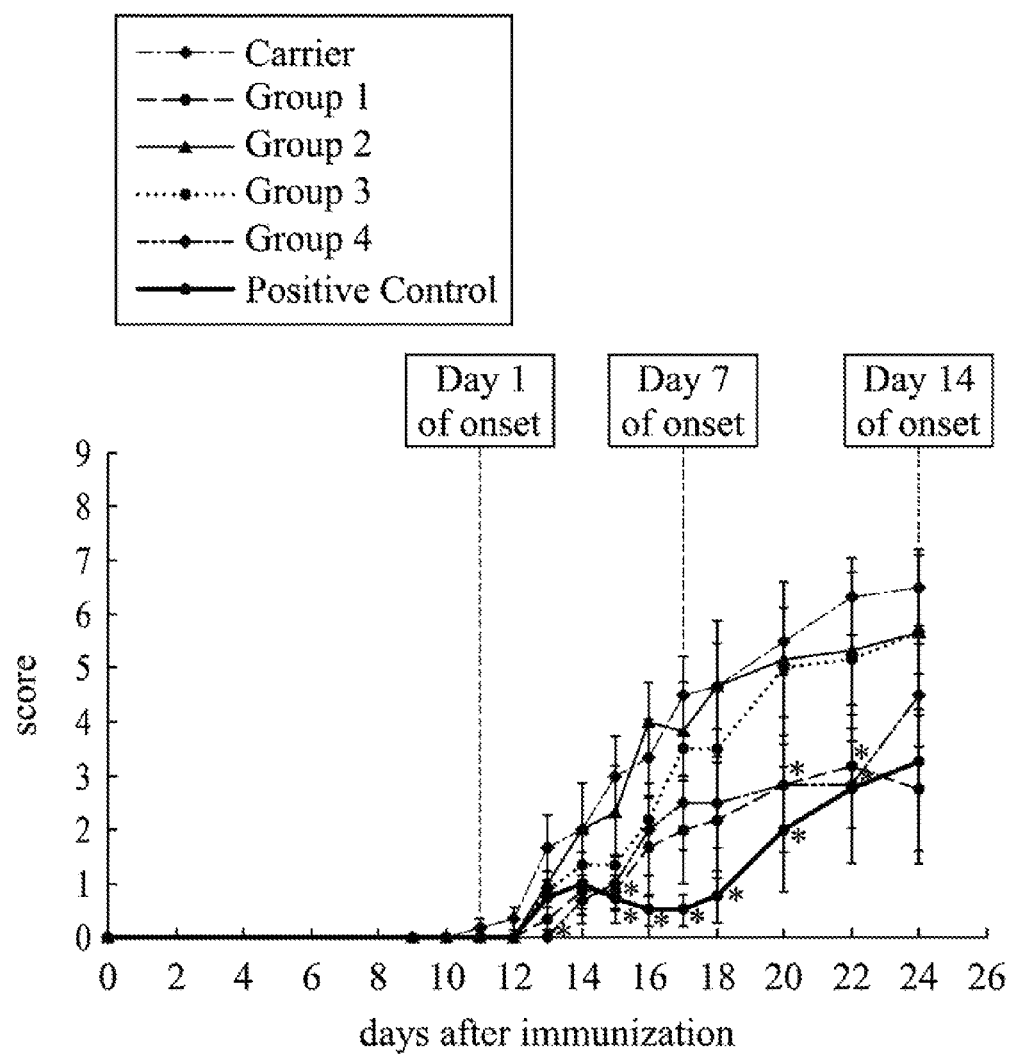
FIG. 17 is the effect of antofine regimes on the arthritis scores in a collagen-induced arthritis model according to one embodiment.

The change of hindpaw volumes of each rat are shown in FIG. 16. The result of arthritis scores are shown in FIG. 17.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method for isolating antofine from a *Cynanchum hancockianum* plant, comprising the steps of:
   (i) mixing a powder of *Cynanchum hancockianum* plant with ethanol to form a first blend;
   (ii) heating the first blend for at least 2 hours at a sufficient temperature and filtering the heated blend to obtain a first extract;
   (iii) concentrating the first extract by evaporation and adding an acid to the concentrated first extract to form a suspension containing a sticky material;
   (iv) filtering the suspension to remove the sticky material and obtain a clear solution;
   (v) extracting the clear solution with dichloromethane to obtain a second extract;
   (vi) concentrating and purifying the second extract by silica gel chromatography and eluting the concentrated purified second extract with ethyl acetate and methanol in a volume ratio of 2:5 to obtain a filtrate;
   (vii) recrystallizing the filtrate to obtain the isolated antofine.

2. The method as claimed in claim 1, wherein the acid comprises hydrochloric acid.

3. The method as claimed in claim 1, wherein the sufficient temperature in the step (ii) is from a temperature of 10° C.~40° C. to boiling temperature of the first blend.

4. The method as claimed in claim 1, wherein the filtering in the step (iv) comprises celite or clay.

5. The method as claimed in claim 1, wherein the antofine is a compound as represented in the following formula

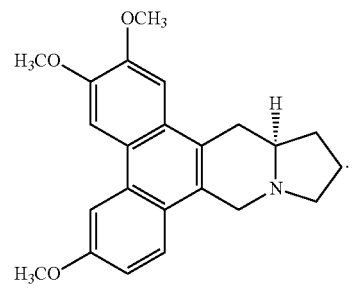 [SMILES: COc1ccc2c3c(c4cc(OC)c(OC)cc4c2c1)C[C@H]1CCCN1C3]

* * * * *